(12) United States Patent
Daniel et al.

(10) Patent No.: US 6,555,321 B1
(45) Date of Patent: Apr. 29, 2003

(54) METHODS FOR DETERMINING CELL RESPONSES THROUGH EPHB RECEPTORS

(75) Inventors: Thomas O. Daniel, Nashville, TN (US); Elke Stein, San Francisco, CA (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/485,653

(22) PCT Filed: Aug. 19, 1998

(86) PCT No.: PCT/US98/17157

§ 371 (c)(1),
(2), (4) Date: Feb. 14, 2000

(87) PCT Pub. No.: WO99/08696

PCT Pub. Date: Feb. 25, 1999

Related U.S. Application Data

(60) Provisional application No. 60/056,164, filed on Aug. 19, 1997.

(51) Int. Cl.$^7$ ...................... G01N 33/53; G01N 33/567; C12N 5/06
(52) U.S. Cl. .................. 435/7.1; 435/7.2; 435/7.21; 435/7.8; 435/334
(58) Field of Search ................ 435/7.1, 7.21, 435/7.8, 7.2, 334

(56) References Cited

U.S. PATENT DOCUMENTS

| | | |
|---|---|---|
| 5,747,033 A | 5/1998 | Davis et al. |
| 5,795,734 A | 8/1998 | Flanagan et al. |

OTHER PUBLICATIONS

Stein et al. "Eph Receptors Discriminate Specific Ligand Oligomers to Determine Alternative Signaling Complexes, Attachment, and Assembly Responses" *Genes & Dev.* 12:667–678, 1998.

Stein et al. "Eph Family Receptors and Ligands in Vascular Cell Targeting and Assembly" *Trends in Cardiovascular Medicine* 7:329–334, 1997.

Stein et al. (Abstract) "Alternative Signaling through ELK subclass Eph receptors is determined by ligand multimerization" American Society of Biochemistry and Molecular Biology, "50 Years of Phosphorylation," Aug. 20, 1997, Seattle, Washington.

Stein et al. (Abstract) "Juxtacrine activation of Eph receptor, ELK, mediates capillary–like endothelial assembly" American Society of Biochemistry and Molecular Biology, "50 Years of Phosphorylation," Aug. 20, 1997, Seattle, Washington.

Daniel et al. (Abstract) "Vascular origin determines endothelial capillary–like assembly responses to different Eph family ligands (LERKs)" International Business Conference, "Angiogenesis Targets: Inhibitors and Inducers," Jul. 24–25, 1997, San Francisco, California.

Martin et al. "Identification of a Subpopulation of Human Renal Microvascular Endothelial Cells With Capacity to Form Capillary–Like Cord and Tube Structures" *In Vitro Cellular and Developmental Biology—Animal* 33:261–269, 1997.

Daniel et al. "ELK and LERK–2 in Developing Kidney and Microvascular Endothelial Assembly" *Kidney Internatl* 50(57):S–73–S–81, 1996.

Stein et al. "Ligand Activation of ELK Receptor Tyrosine Kinase Promotes Its Association with Grb10 and Grb2 in Vascular Endothelial Cells" *J. Biol. Chem.* 38:23588–93, 1996.

Davis et al. "Ligands for EPH–Related Receptor Tyrosine Kinases that Require Membrane Attachment or Clustering for Activity" *Science* 266:816–819, Nov. 4, 1994.

*Primary Examiner*—Christina Chan
*Assistant Examiner*—Maher Haddad
(74) *Attorney, Agent, or Firm*—Needle & Rosenberg, P.C.

(57) ABSTRACT

The present invention provides methods for screening an EphB receptor or an EphB receptor-binding ligand for the ability to promote a selected biological activity when in multimeric form. The invention also provides methods for initiating, promoting, directing, or inhibiting biological activities that involve EphB receptors and/or EphB receptor-binding ligands. The invention further provides compositions that can be used in the foregoing methods.

8 Claims, 7 Drawing Sheets

METHODS FOR DETERMINING CELL RESPONSES THROUGH EPHB RECEPTORS

This application claims the benefit of Provisional Application No. 60/056,164, filed Aug. 19, 1999.

The present invention was funded in part by Public Health Serivce Awards DK8517 and DK47-48 and National Cancer Institute award CA 68485. The government has certain rights in this invention.

BACKGROUND OF THE INVENTION

1. Field of the Invention

The present invention relates to methods and compositions for initiating, promoting and directing cell attachment, migration and cell to cell assembly in response to multimerization of ligands and/or receptors. In particular, the present invention provides multimeric ligands which bind receptors of the Eph receptor tyrosine kinase family to selectively modulate specific cell activities such as cell attachment and cell to cell assembly by promoting the formation of multimeric receptors of specific composition.

2. Background Art

Developmental organization and subsequent remodeling of vasculature obligates vascular endothelial cells and their progenitors to use cell-cell recognition and targeting machinery, both in the initial stages of vasculogenesis and in the angiogenic remodeling required for organogenesis, wound healing and tumor growth. Similar to the developing neural system, vascular cells must migrate, discriminate and assemble with appropriate partner cells to establish and remodel highly integrated and interconnected cellular networks. Early developmental "vasculogenic" assembly of blood vessels requires that endothelial progenitor cells migrate in response to yet unidentified cues, then discriminate among cells they contact to assemble vascular structures with similarly programmed endothelial progenitors (32). During the vascular remodeling occurring during organogenesis, wound healing and tumor growth, endothelial cells in existing vessels receive angiogenic cues to invade their basement membrane and sprout long migrating cellular processes that resemble axons (33,34). Cultured microvascular endothelial cells extend similar processes that track along fibrillar strands of connective tissue matrix to contact and engage appropriate partner cells to form cord and tube structures during in vitro capillary-like morphogenesis. In vivo (and in vitro), these processes encounter and discriminate among cells until appropriate partners for assembly are identified. On engagement of processes extended from existing, efferent limb vessels, specialized interendothelial cellular connections are established to ultimately interconnect lumen (35). This entire scenario is quite similar to the axonal extension, migration, discrimination and targeting processes that direct correct assembly of neural networks.

An enlarging body of evidence has assigned members of the Eph family of receptor tyrosine kinases crucial roles in neural targeting, and early data also support their function in the assembly of vascular structures (1,2,3,7,25). As a class, the Eph family of receptors and their ligands are tissue restricted in their distribution and are highly diverse, with over 13 distinct receptors interacting with distinct ligands. During development, specific Eph family receptors are expressed in distinct tissue sites that are bounded by adjacent tissues expressing their membrane-bound ligands in a reciprocal compartmentation pattern (26). A topographically defined gradient of one ligand, ephrin-A2 (ELF-1), on membranes in the tectum directs the correct targeting of retinal axons that express differential levels of its receptor, EphA3 (Mek 4) (36). Interestingly, regional overexpression of ephrin-A2 (ELF-1) misdirects these projections (37). These and other experiments emphasize the important role these Eph family receptors and ligands play in directing neuronal cell-cell interactions in developing nervous tissue.

Eph family receptors are subdivided into two functional classes by their affinities for membrane-bound ligands of two different structural types. Receptors of the EphA subfamily, including EphA3 (Mek 4), EphA5 (Ehk-1) and others, bind ligands that are membrane-associated through glycerophosphatidylinositol (GPI) linkages, and may be released by phospholipases C and D (41). The GPI-linked ligands characterized to date are ephrin-A1, ephrin-A3, ephrin-A4, ephrin-A2 and ephrin-A5 (formerly called LERKs 1,3,4,6,& 7) (2,7,36,38). The EphB receptor subfamily members show overlapping high affinities for ligands that are transmembrane proteins, including ephrin-B1, ephrin-B2 and ephrin-B3 (formerly called LERKs 2,5 & 8) (9,10,30,39). The transmembrane spanning ligands show remarkable amino acid conservation on the carboxy terminus, implying conservation of structure important in their function, and clouding the distinction between receptors and ligands.

Recent evidence suggests the capacity of these "ligands" to signal through engagement of "receptor" extracellular domains. Engagement of ephrin-B1 ("ligand") by recombinant EphB2 (Nuk) ("receptor") ectodomain initiates tyrosine phosphorylation of ephrin-B1 (28). Moreover, guidance of hippocampal neurons appears directed by their expression of "ligands" for EphB2 (Nuk), a "receptor" ectodomain they engage during the course of decussation through the anterior commissure during development (23). Thus, bidirectional signaling may be initiated by juxtacrine ligand-receptor engagement on cell-cell contact. Such bidirectional signaling is attractive as an intermediate step in cell-cell recognition and commitment to assemble multicellular structures.

Both EphA2 (Eck) and EphB1 (ELK) have been implicated as important intermediaries during angiogenesis. The primary ligand for EphA2 (Eck) was first cloned as a TNFα-induced product of cultured human umbilical vein endothelial cells (ephrin-A1, previously called B-61 or LERK-1) (39,40). Ephrin-A1 is a GPI-linked membrane protein that is also released into a soluble fraction where it may promote migration of bovine endothelial cells through its interaction with EphA2 (Eck) (7). Antibodies against ephrin-A1 interrupt TNFα-induced angiogenic responses in the rat cornea assay, consistent with their interruption of ephrin-A1 to promote angiogenesis through EphA2 (Eck) (7).

EphB1 (ELK) and ephrin-B1 (LERK-2) are both expressed on mesenchymal progenitors of vascular cells, on glomerular capillary endothelial cells in mature kidney and on human umbilical vein endothelial cells (8). The early expression of ephrin-B1 and EphB1 in renal glomerular microvascular progenitor cells has suggested their participation in targeting and capillary assembly in this specialized microcirculation (8). Ephrin-B1 promotes assembly of human renal microvascular endothelial cells (HRMEC) into capillary-like structures (8), yet human umbilical vein endothelial cells (HUVEC) are not responsive, despite their expression of EphB1, and its tyrosine phosphorylation in response to ephrin-B1. In contrast, ephrin-A 1 (LERK-1) has no capillary-assembly activity for HRMEC, yet promotes capillary-like assembly of HUVEC (8). Thus, the downstream signaling responses in vascular endothelial cells from different microcirculations distinguish among Eph receptor ligands to determine different cellular responses.

The present invention provides methods for selectively modulating cell attachment, cell migration, cell to cell assembly and other activities regulated by Eph receptor activation through the promotion or inhibition of multimerization of the receptors which regulate these functions by signal transduction.

SUMMARY OF THE INVENTION

The present invention provides a method for initiating, promoting and/or directing cell attachment to a matrix or to another cell, comprising contacting an EphB receptor-expressing cell with a tetrameric EphB receptor-binding ligand, whereby binding of the tetrameric ligand promotes multimerization of the EphB receptor, thereby initiating, promoting and/or directing cell attachment to a matrix or to another cell.

Also provided is a method for initiating and/or promoting cell migration, comprising contacting an EphB receptor-expressing cell with a tetrameric EphB receptor-binding ligand, whereby binding of the tetrameric ligand promotes multimerization of the EphB receptor, thereby initiating and/or promoting cell migration.

A method for promoting endothelialization of a prosthesis is also provided, comprising contacting the prosthesis with EphB receptor-expressing endothelial cells with a tetrameric EphB receptor-binding ligand whereby binding of the tetrameric ligand promotes multimerization of the EphB receptor, thereby promoting endothelialization of the prosthesis.

In addition, the present invention provides a method for promoting expression of a molecule on the surface of an ephB receptor-expressing cell, wherein the expressed molecule affects leukocyte or platelet attachment and migration, comprising contacting the cell with a tetrameric Eph receptor-binding ligand, whereby binding of the tetrameric ligand promotes multimerization of the EphB receptor, thereby promoting expression of a molecule on the surface of the cell which affects leukocyte or platelet attachment and migration.

Further provided is a method for promoting function of a molecule on the surface of an ephB receptor-expressing cell, wherein the expressed molecule affects leukocyte or platelet attachment and migration, comprising contacting the cell with a tetrameric EphB receptor-binding ligand whereby binding of the tetrameric ligand promotes multimerization of the EphB receptor, thereby promoting function of a molecule on the surface of the cell which affects leukocyte or platelet attachment and migration.

The present invention also provides a method for promoting migration, survival and/or targeting of an EphB receptor-expressing neural cell, comprising contacting the cell with a tetrameric EphB receptor-binding ligand, whereby binding of the tetrameric ligand promotes multimerization of the EphB receptor, thereby promoting migration, survival and/or targeting of the neural cell.

The present invention additionally provides a method for targeting and/or promoting endothelial cell incorporation at a site of endothelial cell injury or new blood vessel formation in a subject, comprising contacting an EphB receptor-expressing endothelial cell at the site of endothelial cell injury or new blood vessel formation in the subject with a tetrameric EphB receptor-binding ligand, whereby binding of the tetrameric ligand promotes multimerization of the receptor, thereby targeting and/or promoting endothelial cell incorporation at the site of endothelial cell injury or new blood vessel formation in the subject.

Furthermore, the present invention provides a method for inhibiting cell attachment to a matrix or to another cell, comprising contacting an EphB receptor-expressing cell, which is stimulated to attach to a matrix or to another cell upon binding a tetrameric Eph receptor-binding ligand, with a substance which prevents binding of the tetrameric ligand to the EphB receptor, thereby inhibiting cell attachment to a matrix or to another cell.

A method for inhibiting cell migration is additionally provided, comprising contacting an EphB receptor-expressing cell, which is stimulated to migrate upon binding a tetrameric EphB receptor-binding ligand, with a substance which prevents binding of the tetrameric ligand to the EphB receptor, thereby inhibiting cell migration.

Additionally provided is a method for inhibiting expression of a molecule on the surface of an EphB receptor-expressing cell, wherein the expressed molecule affects leukocyte or platelet attachment and migration, comprising contacting an EphB receptor-expressing cell, which is stimulated to express a surface molecule which affects leukocyte or platelet attachment and migration upon binding a tetrameric EphB receptor-binding ligand, with a substance which prevents binding of the tetrameric ligand, thereby inhibiting expression of a molecule on the surface of the cell which affects leukocyte or platelet attachment and migration.

The present invention also provides a method for inhibiting function of a molecule on the surface of an EphB receptor-expressing cell, wherein the molecule affects leukocyte or platelet attachment and migration, comprising contacting an EphB receptor-expressing cell, which is stimulated to promote function of a surface molecule which affects leukocyte or platelet attachment and migration upon binding a tetrameric EphB receptor-binding ligand, with a substance which prevents binding of the tetrameric ligand, thereby inhibiting function of a molecule on the surface of the cell which affects leukocyte or platelet attachment and migration.

The present invention additionally provides a method for inhibiting migration, survival and/or targeting of a neural cell which expresses an EphB receptor, comprising contacting an EphB receptor-expressing neural cell, which is stimulated to promote migration, survival or targeting of the neural cell upon binding a tetrameric EphB receptor-binding ligand, with a substance which prevents binding of the tetrameric ligand, thereby inhibiting migration, survival and/or targeting of the neural cell.

The present invention also provides a composition comprising an isolated tetrameric EphB receptor ligand, a composition comprising an isolated tetrameric EphB receptor and a composition comprising an isolated tetrameric EphB receptor ligand/tetrameric EphB receptor complex.

Furthermore, the present invention provides a method for screening an EphB receptor-binding ligand for the ability to initiate, promote and/or direct cell attachment to a matrix or to another cell when in multimeric form, comprising:
a) contacting a multimeric EphB receptor-binding ligand with an EphB receptor-expressing cell under conditions whereby the ligand can bind the receptor; and
b) detecting attachment of cells which have bound multimeric ligand as compared to attachment of cells which have not bound multimeric ligand, whereby attachment of cells which have bound multimeric ligand and no attachment of cells which have not bound multimeric ligand identifies an EphB receptor-binding ligand with the ability to initiate, promote and/or direct cell attachment to a matrix or to another cell when in multimeric form.

A method for screening an EphB receptor-binding ligand for the ability to promote cell migration when in multimeric form is additionally provided, comprising:

a) contacting a multimeric EphB receptor-binding ligand with an EphB receptor-expressing cell under conditions whereby the ligand can bind the receptor; and b) detecting migration of cells which have bound multimeric ligand as compared to migration of cells which have not bound multimeric ligand, whereby migration of cells which have bound multimeric ligand and no migration of cells which have not bound multimeric ligand identifies an EphB receptor-binding ligand with the ability to promote cell migration when in multimeric form.

Also provided is a method for screening an EphB receptor-binding ligand for the ability to promote expression of a molecule on the surface of an EphB receptor-expressing cell, wherein the expressed molecule affects leukocyte or platelet attachment and migration, when in multimeric form, comprising:

a) contacting a multimeric EphB receptor-binding ligand with a cell which expresses an EphB receptor under conditions whereby the ligand can bind the receptor; and b) detecting expression of a molecule which affects leukocyte or platelet attachment and migration on the surface of cells which have bound multimeric ligand as compared to expression of a molecule which affects leukocyte or platelet attachment and migration on the surface of cells which have not bound multimeric ligand, whereby expression of a molecule which affects leukocyte or platelet attachment and migration on the surface of cells which have bound multimeric ligand and no expression of a molecule which affects leukocyte or platelet attachment and migration on the surface of cells which have not bound multimeric ligand identifies a ligand with the ability to promote the expression of a molecule which affects leukocyte or platelet attachment and migration on the surface of cells, when the ligand is in multimeric form.

The present invention further provides a method for screening an EphB receptor-binding ligand for the ability to promote function of a molecule on the surface of an EphB receptor-expressing cell, wherein the function of the molecule affects leukocyte or platelet attachment and migration, when in multimeric form, comprising:

a) contacting a multimeric EphB receptor-binding ligand with an EphB receptor-expressing cell under conditions whereby the ligand can bind the receptor; and b) detecting function of a molecule which affects leukocyte or platelet attachment and migration on the surface of cells which have bound multimeric ligand as compared to function of a molecule which affects leukocyte or platelet attachment and migration on the surface of cells which have not bound multimeric ligand, whereby function of a molecule which affects leukocyte or platelet attachment and migration on the surface of cells which have bound multimeric ligand and no function of a molecule which affects leukocyte or platelet attachment and migration on the surface of cells which have not bound multimeric ligand identifies a ligand with the ability to promote function of a molecule which affects leukocyte or platelet attachment and migration on the surface of cells, when the ligand is in multimeric form.

The present invention also provides a method for screening an EphB receptor-binding ligand for the ability to promote migration, survival and/or targeting of a neural cell when in multimeric form, comprising:

a) contacting a multimeric EphB receptor-binding ligand with an EphB receptor-expressing neural cell under conditions whereby the ligand can bind the receptor; and b) determining migration, survival and/or targeting of a neural cell which has bound multimeric ligand as compared to migration, survival or targeting of a neural cell which has not bound multimeric ligand, whereby migration, survival or targeting of a neural cell which has bound multimeric ligand and no migration, survival, or targeting of a neural cell which has not bound multimeric ligand identifies a ligand with the ability to promote migration, survival or targeting of a neural cell when in multimeric form.

Additionally provided is a method for screening an EphB receptor for the ability to initiate, promote and/or direct cell attachment to a matrix or to another cell when the receptor is in multimeric form, comprising:

a) producing a multimeric EphB receptor on the surface of a cell which expresses an EphB receptor; and b) detecting attachment of cells with a multimeric EphB receptor as compared to attachment of cells without a multimeric EphB receptor, whereby attachment of cells with a multimeric EphB receptor and no attachment of cells without a multimeric EphB receptor identifies an EphB receptor with the ability to initiate, promote and/or direct cell attachment to a matrix or to another cell when in multimeric form.

Further provided is a method for screening an EphB receptor for the ability to promote cell migration when the receptor is in multimeric form, comprising:

a) producing a multimeric EphB receptor on the surface of a cell which expresses an EphB receptor; and b) detecting migration of cells with a multimeric EphB receptor as compared to migration of cells without a multimeric EphB receptor, whereby migration of cells with a multimeric EphB receptor and no migration of cells without a multimeric EphB receptor identifies an EphB receptor with the ability to promote cell migration when in multimeric form.

The present invention also provides a method for screening an EphB receptor for the ability to promote expression of a molecule on the surface of an EphB receptor-expressing, wherein the expressed molecule affects leukocyte or platelet attachment and migration, when the receptor is in multimeric form, comprising:

a) producing a multimeric EphB receptor on the surface of a cell which expresses an EphB receptor; and b) detecting expression of a molecule which affects leukocyte or platelet attachment and migration on the surface of cells with a multimeric EphB receptor as compared to expression of a molecule which affects leukocyte or platelet attachment and migration on the surface of cells without a multimeric EphB receptor, whereby expression of a molecule which affects leukocyte or platelet attachment and migration on the surface of cells with a multimeric EphB receptor and no expression of a molecule which affects leukocyte or platelet attachment and migration on the surface of cells without a multimeric EphB receptor identifies an EphB receptor with the ability to promote expression of a molecule on the surface of a cell which expresses an EphB receptor, wherein the expressed molecule affects leukocyte or platelet attachment and migration, when the EphB receptor is in multimeric form.

The present invention additionally provides a method for screening an Eph receptor for the ability to promote function of a molecule on the surface of an EphB receptor-expressing cell, wherein the function of the molecule affects leukocyte or platelet attachment and migration, when the receptor is in multimeric form, comprising:

a) producing a multimeric EphB receptor on the surface of a cell which expresses an EphB receptor; and b) detecting function of a molecule which affects leukocyte or platelet attachment and migration on the surface of cells with a multimeric EphB receptor as compared to function of a molecule which affects leukocyte or platelet attachment and migration on the surface of cells without a multimeric EphB receptor, whereby function of a molecule which affects leukocyte or platelet attachment and migration on the surface of cells with a multimeric EphB receptor and no function of a molecule which affects leukocyte or platelet attachment and migration on the surface of cells without a multimeric EphB receptor identifies an EphB receptor with the ability to promote function of a molecule on the surface of a cell which expresses an EphB receptor, wherein the expressed molecule affects leukocyte or platelet attachment and migration, when the EphB receptor is in multimeric form.

A method for screening an EphB receptor for the ability to promote migration, survival and/or targeting of a neural cell when the receptor is in multimeric form is also provided, comprising:

a) producing a multimeric EphB receptor on the surface of a neural cell which expresses an EphB receptor; and b) detecting migration, survival or targeting of neural cells with a multimeric EphB receptor as compared to migration, survival or targeting of neural cells without a multimeric EphB receptor, whereby migration, survival and/or targeting of neural cells with a multimeric EphB receptor and no migration, survival or targeting of neural cells without a multimeric EphB receptor identifies an EphB receptor with the ability to promote migration, survival and/or targeting of neural cells when in multimeric form.

In addition, the present invention provides a method for screening a substance for the ability to inhibit the binding of a multimeric EphB receptor-binding ligand to an EphB receptor comprising:

a) contacting the substance with a cell expressing an EphB receptor;

b) contacting the cell of step (a) with a multimeric EphB receptor-binding ligand under conditions whereby the multimeric ligand can bind the receptor; and c) detecting the binding of the multimeric ligand to the receptor, whereby no binding of the multimeric ligand to the receptor identifies a substance with the ability to inhibit the binding of a multimeric EphB receptor-binding ligand to an EphB receptor.

Also provided herein is a method for promoting angiogenesis, comprising contacting EphB receptor-expressing cells which are associated with angiogenesis with a multimeric EphB receptor-binding ligand, whereby binding of the tetrameric ligand promotes multimerization of the EphB receptor, thereby promoting angiogenesis.

A method for disrupting angiogenesis is additionally provided, comprising contacting an EphB receptor-expressing cell which promotes angiogenesis upon binding a multimeric EphB receptor-binding ligand with a substance which prevents formation of a multimeric EphB receptor-binding ligand or inhibits binding of the multimeric EphB receptor-binding ligand to the receptor, thereby disrupting angiogenesis Further provided is a method for treating a disease associated with pathological angiogenesis in a subject, comprising contacting an EphB receptor-expressing cell of the subject which promotes angiogenesis upon binding a tetrameric EphB receptor-binding ligand with a substance which prevents binding of the tetrameric ligand, thereby disrupting angiogenesis and treating a disease associated with pathological angiogenesis.

The present invention also provides a method for treating a condition associated with interruption of angiogenic processes in a subject, comprising contacting an EphB receptor-expressing cell of the subject with a tetrameric EphB receptor-binding ligand, whereby binding of the tetrameric ligand promotes multimerization of the EphB receptor, thereby promoting angiogenesis and treating a condition associated with interruption of angiogenic processes.

The present invention additionally provides a method for screening a substance for the ability to inhibit angiogenesis, comprising:

a) contacting the substance with a cell expressing an EphB receptor;

b) contacting the cell of step (a) with a multimeric EphB receptor-binding ligand, which promotes angiogenesis, under conditions whereby the multimeric ligand can bind the receptor; and c) detecting angiogenesis in cells contacted with the substance, as compared to angiogenesis in cells not contacted with the substance, whereby no angiogenesis in cells contacted with the substance and angiogenesis in cells not contacted with the substance identifies a substance having the ability to inhibit angiogenesis.

Finally, the present invention provides a method for screening an EphB-receptor binding ligand for the ability to promote angiogenesis when in multimeric form, comprising:

a) contacting a multimeric EphB receptor-binding ligand with a cell which expresses an EphB receptor under conditions whereby the ligand can bind the receptor; and b) detecting angiogenesis of cells which have bound multimeric ligand as compared to angiogenesis of cells which have not bound multimeric ligand, whereby angiogenesis of cells which have bound multimeric ligand and no angiogenesis of cells which have not bound multimeric ligand identifies an EphB receptor-binding ligand with the ability to promote angiogenesis when in multimeric form.

BRIEF DESCRIPTION OF THE DRAWINGS

FIG. 1A: In an in vitro angiogenesis assay, HRMEC (12) were plated on Matrigel-coated dishes in defined medium in the absence (NA), or presence of indicated agonists, including phorbol myristate acetate (PMA, 20 ng ml$^{-1}$). Ephrin-B1/Fc (at indicated concentrations) or a control Fc fusion protein, ORF/Fc (9) (500 ng ml$^{-1}$), were presented as either dimers, or preclustered multimers (+anti-Fc). Cells were photographed 8 h after plating. Insert: Phosphotyrosine immunoblots of EphB1 immunoprecipitates from HRMEC plated on Matrigel-coated dishes. FIG. 1B: Attachment of HRMEC to either Matrigel- or fibronectin-coated dishes 90 min after plating in medium supplemented with dimeric or multimeric (+anti-Fc) Fe fusion proteins. (Mean +/− SEM of three independent determinations are displayed (*p<0.05, p<0.001, *p<0.0001)). FIG. 1C: Attachment of P19 cells to fibronectin coated dishes and phosphotyrosine immunoblots of EphB1 (insert) after plating in medium supplemented with dimeric, or multimeric (+anti-Fc), ORF/Fc or ephrin-B1/Fc.

FIG. 2A: Ephrin-B1/Fc dimers (ephrin-B1/Fc, 50 μg) or preclustered multimers (ephrin-B1/Fc, 50 μg+anti-Fc, 5 μg) were separated by exclusion chromatography in PBS on a Sepharose 6 column (Pharmacia) calibrated with standards of 445 kDa (ferritin), 272 kDa (urease) and 150 kDa (IgG). FIGS. 2B and 2C: Fractions containing 500 ng ml$^{-1}$ protein from the indicated $A_{278}$ peaks (Fxn "A," Fxn "B," Fxn "C") were analyzed for activity to promote tyrosine phosphorylation of EphB1 and recruitment of LMW-PTP to EphB1 complexes (FIG. 2B) and to promote attachment of HRMEC and P19 cells (FIG. 2C). Complex stoichiometry was confirmed by comparison of each fraction to mixed standards of Ephrin-B1/Fc and anti-Fc separated by SDS-PAGE, transferred to Immobilon-P and stained with amido black. Tetramers (one anti-Fc molecule complexing two ephrin-B1/Fe dimers) showed activity in both assays.

FIG. 3A: Microvascular endothelial attachment to fibrinogen is stimulated by precoating of surfaces with nitrocellulose-bound ephrin-B1/Fc. EphrinB1/Fc (300 ng/cm$^2$ surface area) was adsorbed overnight at 4° C. to 48-well plates precoated with either nitrocellulose, fibrinogen, or both, in combination with ephrin-B1/Fe (300 ng/cm$^2$) or an Fc control, human IgG$_1$ (300 ng/cm$^2$), as indicated. Wells were washed, blocked with solution containing 1% bovine albumin, plated with 7×10$^5$ endothelial cells for 1 h, then assayed for cell attachment, as described herein. FIG. 3B: Effect of adsorbed fibrinogen density on endothelial attachment. Indicated amounts of fibrinogen were adsorbed to surfaces coated with no additive (Fbg alone) or ephrinB1/Fe (300 ng/cm$^2$), and endothelial attachment was assayed, as described herein. FIG. 3C: Adsorbed ephrin-B1/Fc density effect on endothelial attachment.

Figure 1A:
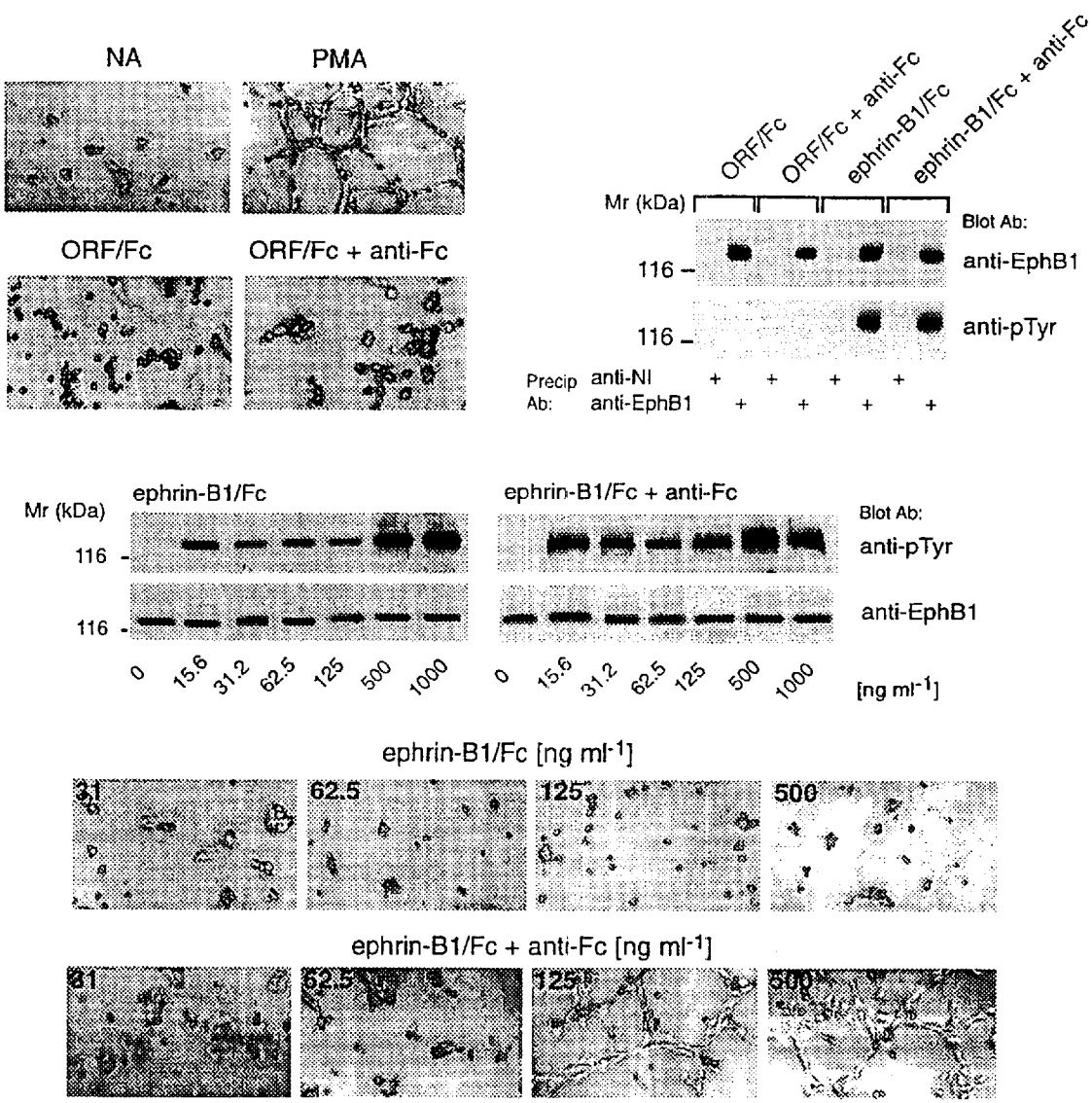
FIGS. 1A, 1B and 1C. Ligand multimers elicit different responses.

Indicated amounts of ephrin-B1/Fc were adsorbed to surfaces coated with fibrinogen (2 mg/cm$^2$), and endothelial attachment was assayed, as described herein. EphB1 receptor activation was determined by phosphotyrosine immunoblot of immunoprecipitated EphB1 receptors.

DETAILED DESCRIPTION OF THE INVENTION

The present invention provides the surprising discovery that distinctions among ligand multimers are critical determinants of biological response such as cell attachment, cell migration and cell to cell assembly. Thus, the methods of this invention provide for the formation of ligand multimers which promote the formation of receptor multimers on the surface of cells for inducing specific biological responses. It is understood that in these methods, multimeric receptors can be produced by binding multimeric ligands as well as by any other mechanism or with any other substance which can produce multimeric receptors.

Thus, the present invention provides a method for initiating, promoting and/or directing cell attachment, comprising contacting cells with a substance which promotes multimerization of receptors associated with initiating, promoting and/or directing cell attachment. Thus, it is understood that the method of this invention provides for one or more of the processes of initiation, promotion and direction as these processes pertain to cell attachment. The substance can be a multimeric ligand and in a preferred embodiment can be a tetrameric ligand and the multimerization of the receptor can result in the formation of tetrameric receptors. The multimeric ligand can also be a multimer of ligands greater than four which promotes multimerization of receptors.

Further provided is a method for initiating and promoting cell migration comprising contacting cells with a substance which promotes multimerization of receptors associated with initiating and promoting cell migration. The substance can be a multimeric ligand such as a tetrameric ligand which promotes the formation of tetrameric receptors. The cells can be contacted with the substance in vivo or ex vivo as described above.

In addition, the present invention provides a method for promoting cell to cell assembly, comprising contacting cells with a substance which promotes multimerization of receptors associated with cell to cell assembly. The substance can be a multimeric ligand such as a tetrameric ligand which promotes the formation of tetrameric receptors. The cells can be contacted with the substance in vivo or ex vivo as described above.

Further provided is a method for producing multimeric receptors comprising contacting receptors with a substance which promotes multimerization. The receptors can be isolated according to methods standard in the art or the receptors can be on the surface of cells. The substance which promotes multimerization of receptors can be a multimeric ligand, such as a tetrameric ligand which produces tetrameric receptors. In addition, the multimeric receptors can be produced in vivo, ex vivo or in vitro.

The receptor associated with cell migration, cell attachment and cell to cell assembly can be a member of the ELK receptor family, which can be, but is not limited to member of the Eph receptor subclass, such as EphA1, EphA2, EphA3, EphA4, EphA5, EphA6, EphA7, EphA8, EphB1, EphB2, EphB3, EphB4 and EphB5.

The ligand which can be used to promote multimerization of receptors can be, but is not limited to, ephrin-A1, ephrin-A2, ephrin-A3, ephrin-A4, ephrin-A5, ephrin-B1, ephrin-B2 and ephrin-B3.

Thus, the present invention also provides a method for initiating, promoting and/or directing the attachment and differentiation of cells, comprising contacting cells with a ligand which initiates, promotes and/or directs the attachment and differentiation of cells when in multimeric form. The ligand multimers can initiate, promote and/or direct these activities by producing multimeric receptors which are activated when in multimeric form to trigger these activities in the cell. The ligand multimers of the present invention are preferably tetramers, but can be multimers of greater numbers, such as octamers, etc., which initiate, promote and/or direct the attachment and differentiation of cells. Alternatively, the ligand multimers of this invention can block the initiation, promotion and/or direction of cell attachment and differentiation of cells.

Furthermore, the present invention provides a method for initiating and/or promoting cell migration, comprising contacting cells with a ligand which initiates and/or promotes cell migration when in multimeric form. The ligand multimers can initiate and/or promote cell migration by producing multimeric receptors which are activated when in multimeric form to trigger cell migration. The ligand multimers of the present invention are preferably tetramers, but can be multimers of greater numbers which initiate and/or promote cell migration. Alternatively, the ligand multimers of this invention can block the initiation and/or promotion of cell migration.

Also provided is a method for promoting cell to cell assembly, comprising contacting cells with a ligand which promotes cell to cell assembly when in multimeric form. The multimeric ligand can promote cell to cell assembly by promoting the formation of multimeric receptors which activate cell to cell assembly upon formation into multimeric receptors. As stated above, the ligand multimers can be tetramers or larger multimers which promote cell-cell assembly. Alternatively, the ligand multimers of this invention can block the promotion of cell to cell assembly.

In particular, the present invention provides a method for initiating, promoting and/or directing cell attachment to a matrix or to another cell, comprising contacting an EphB receptor-expressing cell with a tetrameric EphB receptor-binding ligand which promotes multimerization of the receptor, whereby binding of the tetrameric ligand promotes multimerization of the EphB receptor, thereby initiating, promoting and/or directing cell attachment to a matrix or to another cell.

As used herein, "matrix" can mean any solid or semi-solid surface or substrate, which can be either biological or non-biological, to which a cell can attach, as would be well known in the art. Examples of a matrix of this invention can include, but is not limited to, peptides containing an RGD sequence], vitronectin, fibrinogen, fibronectin and like compounds, as would be known to one of skill in the art.

The present invention also provides a method for initiating and promoting cell migration, comprising contacting an EphB receptor-expressing cell with a tetrameric EphB receptor-binding which promotes multimerization of the receptor, whereby binding of the tetrameric ligand promotes multimerization of the EphB receptor, thereby initiating and promoting cell migration.

The EphB receptor of these methods can be EphB1 or EphB2 and the ligand of this method can be ephrinB1 or ephrinB2. In addition, the cells of these methods can be, but are not limited to, epithelial cells, endothelial cells, neuron progenitor cells, fibroblasts, embryonic kidney cells and teratocarcinoma cells.

For the purposes of the present invention, cell to cell assembly, cell attachment and cell migration are distinct from cell proliferation and tyrosine phosphorylation. Also, as used herein, the term "binding" describes the interaction between a receptor and a ligand specific for that receptor; "signaling" describes cellular events or processes which are mediated by binding of ligand to receptor; and "attachment" describes the interaction between a cell and a matrix or between a cell and another cell.

The cells of the present invention can include, but are not limited to, mature and progenitor forms of cells with differentiated characteristics of neurons of all types, endothelial, pericyte, smooth muscle and vascular cells, osteoclasts and osteoblasts, epithelial cell types including keratinocytes, intestinal and other alimentary epithelial cells and corneal epithelial cells.

Furthermore, the cells can be contacted with the substance which promotes these activities by producing multimeric ligands and receptors either in vivo or ex vivo. For in vivo administration, the substance can be administered to any subject having cells which express the receptors of this invention. The subject can be an animal and is preferably a human. The substance can be administered to the subject in a pharmaceutically acceptable carrier and can be orally or parenterally administered to the subject. By "pharmaceutically acceptable" is meant a material that is not biologically or otherwise undesirable, i.e., the material may be administered to a subject along with the selected substance without causing any undesirable biological effects or interacting in a deleterious manner with any of the other components of the pharmaceutical composition in which it is contained.

Suitable carriers for parenteral administration of the substance in a sterile solution or suspension can include sterile saline that may contain additives, such as ethyl oleate or isopropyl myristate, and can be injected, for example, intravenously, as well as into subcutaneous or intramuscular tissues.

Suitable carriers for oral administration include one or more substances which may also act as flavoring agents, lubricants, suspending agents, or as protectants. Suitable solid carriers include calcium phosphate, calcium carbonate, magnesium stearate, sugars, starch, gelatin, cellulose, carboxypolymethylene, or cyclodextrans. Suitable liquid carriers may be water, pyrogen free saline, pharmaceutically accepted oils, or a mixture of any of these. The liquid can also contain other suitable pharmaceutical additions such as buffers, preservatives, flavoring agents, viscosity or osmoregulators, stabilizers or suspending agents. Examples of suitable liquid carriers include water with or without various additives, including carboxypolymethylene as a pH-regulated gel.

The substance which promotes these activities by producing multimeric receptors and ligands can be administered to the subject in amounts sufficient to modulate the activity of the receptor in the subject as desired. Optimal dosages used will vary according to the individual, on the basis of age, size, weight, condition, etc., as well as the particular modulating effect being induced. One skilled in the art will realize that dosages are best optimized by the practicing physician and methods for determining dosage are described, for example, in *Remington's Pharmaceutical Sciences* (31). Treatment can be continued for an indefinite period of time, as indicated by monitoring of the signs, symptoms and clinical parameters associated with a particular activity of the receptor.

The ligands of this invention which initiate, promote and/or direct cell attachment and/or initiate and promote cell migration, cell differentiation and/or cell-cell assembly can be, but are not limited to, ephrin-A1, ephrin-A2, ephrin-A3, ephrin-A4, ephrin-A5, ephrin-B1, ephrin-B2 and ephrin-B3, as well as any other ligand now known or identified in the future to initiate, promote and direct the attachment, migration and differentiation of cells and/or promote cell-cell assembly, particularly by promoting multimerization of the receptors which trigger these activities.

It is also understood that the receptors and ligands of the present invention can be adfixed to solid surfaces to carry out the methods of this invention. For example, the receptors and ligands can be engineered with adapters which allow them to be adfixed to a solid surface as multimers, such as a prosthetic vascular graft and endothelial cells can be added to the graft, allowing for the biological processes of cell attachment, cell migration and cell to cell assembly to proceed on the solid surface as facilitated by the presence of the multimeric ligands and receptors. The differential activity of tetrameric and dimeric ligands on a solid surface is described in the Examples section provided herein.

Thus, the present invention also provides a method for promoting endothelialization of a prosthesis, comprising contacting the prosthesis with endothelial cells and a ligand which promotes endothelialization of cells when in multimeric form under conditions whereby binding of the ligand to the cells can occur and endothelialization is promoted. Specifically, the present invention provides a method for promoting endothelialization of a prosthesis, comprising contacting the prosthesis with EphB receptor-expressing endothelial cells with a tetrameric EphB receptor-binding ligand which promotes multimerization of the EphB receptor, whereby binding of the tetrameric ligand promotes multimerization of the EphB receptor, thereby promoting endothelialization of the prosthesis.

As used herein, "endothelialization" means the process by which a confluent and continuous endothelial monolayer assembles, either de novo or in repair of inflicted damage. Endothelialization also means the spreading and attachment of endothelial cells to a prosthetic surface to promote spreading and covering the surface with an endothelial monolayer. The multimeric ligands can promote endothelialization of a prosthesis by promoting multimerization of receptors which promote endothelialization when in multimeric receptor form. Also as used herein, "prosthesis" means any biologically acceptable material which can be used to replace, restore or facilitate a biological function. For example, the prosthesis of this invention can be a GORTEX endovascular graft, or other similar materials as would be well known in the art.

Furthermore, the present invention provides methods for promoting migration and attachment of cells, as well as methods for promoting expression of surface molecules affecting leukocyte or platelet attachment and migration.. All of these methods comprise contacting cells of the subject with a ligand which promotes migration and attachment of cells and/or promotes expression of surface molecules affecting leukocyte or platelet attachment and migration when in multimeric (e.g., tetrameric) form. The multimeric ligands can promote these activities in cells by promoting multimerization of receptors which promote these activities when in multimeric receptor form.

Specifically, provided herein is a method for promoting expression of a molecule on the surface of an ephB receptor-expressing cell, wherein the expressed molecule affects leukocyte or platelet attachment and migration, comprising contacting the cell with a tetrameric EphB receptor-binding ligand which promotes multimerization of the EphB receptor, whereby binding of the tetrameric ligand promotes multimerization of the EphB receptor, thereby promoting expression of a molecule on the surface of the cell which affects leukocyte or platelet attachment and migration. The receptor of this method can be EphB1 and the ligand of this method can be ephrin-B1.

The present invention also provides a method for promoting function of a molecule on the surface of an ephB receptor-expressing cell, wherein the expressed molecule affects leukocyte or platelet attachment and migration, comprising contacting the cell with a tetrameric ligand which binds an EphB receptor and promotes multimerization of the EphB receptor, whereby multimerization of the EphB receptor promotes function of a molecule on the surface of the cell which affects leukocyte or platelet attachment and migration, under conditions whereby the tetrameric ligand can bind the EphB receptor and promote multimerization of the EphB receptor, thereby promoting function of a molecule on the surface of the cell which affects leukocyte or platelet attachment and migration. The receptor of this method can be EphB1 and the ligand of this method can be ephrin-B1.

As used herein, a molecule which affects leukocyte or platelet attachment or migration is a molecule which can initiate, promote and/or direct leukocyte or platelet attachment or migration, as well as a molecule which can inhibit and/or disrupt leukocyte or platelet attachment. Such molecules are well known in the art. For example, the molecule on the surface of a cell which affects leukocyte or platelet attachment and migration as set forth in this invention can be, but is not limited to, $\alpha_v\beta_3$, $\alpha_5\beta_1$, ICAM-1 and E-selectin.

The methods described above for promoting these various activities can be directed to specific locations in a subject. For example, the above-listed activities can be promoted according to the methods of the present invention in any tissues which include vascular and neural cells. In particular, the specific location could be tumor beds, renal glomeruli, central nervous system capillaries, or any location at which the promotion of these activities would be desirable.

A method is also provided herein for stimulating endothelial cell attachment, migration and/or cell to cell assembly, comprising contacting endothelial cells with a ligand which stimulates endothelial cell attachment and migration when in multimeric (e.g., tetrameric) form. The ligand can be any of the ligands of the present invention which have been shown to stimulate endothelial cell attachment and migration when in multimeric form. The endothelial cells can be any of the endothelial cells of the present invention which can be stimulated to attach and migrate upon contact with the multimeric ligands of this invention. The mechanism by which the multimeric ligands stimulate endothelial cell attachment and migration can be by promoting multimerization of receptors which promote endothelial cell attachment and migration when in multimeric receptor form.

The present invention further provides a method for initiating, promoting and directing the attachment, migration, differentiation and repair of neural cells, comprising contacting neural cells with a ligand with initiates, promotes and directs the attachment, migration, differentiation and repair of neural cells when in multimeric form. As used herein, "repair of neural cells" means integration to the extent that normal function of a damaged neural cell is recovered. The multimeric ligands can initiate, promote and direct these activities in cells by promoting multimerization of receptors associated with these activities and which are activated to promote these activities in cells when in multimeric receptor form.

Thus, the present invention further provides a method for promoting migration, survival and/or targeting of an EphB receptor-expressing neural cell, comprising contacting the cell with a tetrameric EphB receptor-binding ligand which promotes multimerization of the EphB receptor, whereby binding of the tetrameric ligand promotes multimerization of the EphB receptor, thereby promoting migration, survival or targeting of the neural cell. The receptor of any of these methods can be EphB1 and the ligand of this method can be ephrin-B1.

Also provided in the present invention is a method for treating endothelial cell injury in a subject, comprising contacting a site of endothelial cell injury in the subject with a ligand which stimulates endothelial cell attachment and migration when present in multimeric form. As used herein, "endothelial cell injury" is damage or injury to an endothelial cell which causes disruption of normal function and viability.

The endothelial cell injury can be in any of the endothelial cells of the present invention and can be the result of a variety of conditions including, but not limited to, hypoxic insult, thermal insult, immunological insult and toxic insult. Such injury can also be the result of an interruption of angiogenic processes due to a variety of conditions, such as, for example, cancer, inflammatory arthritis, thrombotic microangiopathies, diabetes, hypertension, viral and rickettsial diseases, peripheral vascular disease, atherosclerotic vascular disease and the like. The treatment of endothelial cell injury by multimeric ligand contact at the site of injury can be via a mechanism of promoting multimerization of receptors associated with repair of endothelial cell injury which are activated to initiate the repair response when in multimeric receptor form.

Thus, the present invention further provides a method for targeting and promoting endothelial cell incorporation at a site of endothelial cell injury or new blood vessel formation in a subject, comprising contacting an EphB receptor-expressing endothelial cell at the site of endothelial cell injury or new blood vessel formation in the subject with a tetrameric EphB receptor-binding ligand which promotes multimerization of the EphB receptor, whereby binding of the tetrameric ligand promotes multimerization of the receptor, thereby targeting and promoting endothelial cell incorporation at the site of endothelial cell injury or new blood vessel formation in the subject. The receptor of this method can be EphB1 and the ligand of this method can be ephrin-B1.

In a further embodiment, the present invention also provides methods for inhibiting the above-listed activities promoted by the multimeric ligands of this invention, comprising contacting multimeric ligands with a substance which disrupts the ligand (e.g., antibodies, modified Eph receptor ectodomains or other substances which can disrupt the multimer or inhibit multimer formation), thereby inhibiting the formation of multimeric receptors and thus, the multimeric receptor-promoted activity. The mechanism by which these activities can be inhibited can be by disrupting multimeric receptors or preventing the formation of multimeric receptors, thereby inhibiting multimeric receptor-promoted activity. It is also contemplated that the multimeric ligands and receptors themselves may inhibit these activities.

The present invention also provides a method for inhibiting cell attachment, comprising contacting cells which are stimulated to attach upon binding a ligand which promotes cell attachment when in multimeric form, with a substance which prevents binding of the ligand. Such a substance can be an antibody which binds the receptor or which binds the ligand, having the net effect of preventing binding of the ligand and receptor. Other substances can include proteins, peptides, or other molecules which interfere with the binding of ligand and receptor, either directly or indirectly. For example, the substance can be a dimeric ligand which has antagonistic activity, as well as other small molecules which interrupt the receptor interfaces that engage in multimer binding to activate Eph receptor in oligomeric forms that do not permit the signals evoked by ligand multimers to be generated (i.e., a pseudo-agonist effect). Additionally, the substance can be a ligand or receptor ectodomain which binds its respective target and occupies the necessary binding site, thereby inhibiting the binding of ligand and receptor.

In addition, the inhibition of cell attachment can be by disrupting multimeric receptors which promote or maintain cell attachment, as well as by inhibiting the formation of multimeric receptors associated with cell attachment. Such inhibition can be induced by contacting the receptors with a substance that disrupts or inhibits formation of multimeric receptors. The substance can be, for example, a substance, as described above, which disrupts or inhibits the formation of multimeric ligands or which disrupts or inhibits receptor/ligand binding.

Further provided is. a method for inhibiting cell-cell assembly, comprising contacting cells which are stimulated to assemble upon binding a ligand which promotes cell-cell assembly when in multimeric form, with a substance which prevents binding of the ligand. The inhibition of cell to cell assembly may be by inhibiting the formation of multimeric receptors which promote cell to cell assembly when in multimeric receptor form.

The present invention also provides a method for inhibiting cell migration, comprising contacting cells which are stimulated to migrate upon binding a ligand which promotes cell migration when in multimeric form, with a substance which prevents binding of the ligand. The inhibition of cell migration may be by inhibiting the formation of multimeric receptors which promote cell migration when in multimeric receptor form.

In the same context, the present invention also contemplates methods for inhibiting migration of cells and/or expression of surface molecules affecting leukocyte attachment and migration in a subject comprising contacting cells of the subject with a substance which prevents binding of a ligand which promotes migration and/or expression of surface molecules affecting leukocyte attachment and migration in a subject when in multimeric form.

Also provided is a method for inhibiting endothelial cell attachment, migration and/or cell to cell assembly, comprising contacting endothelial cells with a substance which prevents binding of a ligand which promotes endothelial cell attachment, migration and/or cell to cell assembly when in multimeric form.

In addition, a method is provided for inhibiting or interrupting neural cell migration and repair, comprising contacting neural cells with a substance which prevents binding of a ligand which promotes neural cell migration and repair when in multimeric form.

In a particular embodiment, the present invention provides a method for inhibiting cell attachment to a matrix or to another cell, comprising contacting an EphB receptor-expressing cell, which is stimulated to attach to a matrix or to another cell upon binding a tetrameric Eph receptor-binding ligand, with a substance which prevents formation of a tetrameric ligand or prevents formation of a tetrameric receptor or prevents binding of a tetrameric ligand to the EphB receptor, thereby inhibiting cell attachment to a matrix or to another cell.

Also provided is a method for inhibiting cell migration, comprising contacting an EphB receptor-expressing cell, which is stimulated to migrate upon binding a tetrameric EphB receptor-binding ligand, with a substance which prevents formation of a tetrameric ligand, formation of a tetrameric receptor or binding of a tetrameric ligand to the EphB receptor, thereby inhibiting cell migration.

Furthermore, the present invention provides a method for inhibiting expression and/or function of a molecule on the surface of an EphB receptor-expressing cell, wherein the expression and/or promotion of function of the molecule affects leukocyte or platelet attachment and migration, comprising contacting an EphB receptor-expressing cell, which is stimulated to express or promote function a surface molecule which affects leukocyte or platelet attachment and migration upon binding a tetrameric EphB receptor-binding ligand, with a substance which prevents formation of a tetrameric ligand or prevents formation of a tetrameric receptor or prevents binding of a tetrameric ligand to the EphB receptor, thereby inhibiting expression and/or function of a molecule on the surface of the cell which affects leukocyte or platelet attachment and migration.

A method for inhibiting migration, survival or targeting of a neural cell which expresses an EphB receptor is also provided herein, comprising contacting an EphB receptor-expressing neural cell, which is stimulated to promote migration, survival or targeting of the neural cell upon binding a tetrameric EphB receptor-binding ligand, with a substance which prevents formation of a tetrameric ligand or prevents formation of a tetrameric receptor or prevents binding of a tetrameric ligand to the EphB receptor, thereby inhibiting migration, survival or targeting of the neural cell.

The above described methods for inhibiting various cell activities can be by disrupting or inhibiting the formation of multimeric receptors which promote or maintain these activities when present in the cells in multimeric receptor form. The inhibition can be caused by a substance which can be an antibody which binds the receptor or which binds the ligand, having the net effect of preventing binding of the ligand and receptor. Other substances can include proteins, peptides, or other molecules which interfere with the binding of ligand and receptor, either directly or indirectly. For example, the substance can be a dimeric ligand which has antagonistic activity, as well as other small molecules which interrupt the receptor interfaces that engage in multimer binding to activate Eph receptor in oligomeric forms that do not permit the signals evoked by ligand multimers to be generated (i.e., a pseudo-agonist effect). Additionally, the substance can be a ligand or receptor ectodomain which binds its respective target and occupies the necessary binding site, thereby inhibiting the binding of ligand and receptor.

In addition, the present invention provides an isolated multimeric Eph receptor binding ligand having more than two ligand subunits. For example, the multimeric Eph receptor ligand can have four ligand subunits, six ligand subunits, eight ligand subunits, etc. It is further contemplated that the multimeric Eph receptor ligand can be bound to a receptor protein, thus providing a multimeric Eph receptor ligand/receptor complex, which can be an isolated complex. Thus, the present invention specifically provides a composition comprising an isolated tetrameric EphB receptor ligand, a composition comprising an isolated tetrameric EphB receptor and a composition comprising an isolated tetrameric EphB receptor ligand/tetrameric EphB receptor complex. The composition of this invention can be a tetrameric EphB1 receptor or a tetrameric EphB2 receptor or a tetrameric EphB3 receptor. The composition of this invention can also be a tetrameric ephrin-B1 ligand, a tetrameric ephrin-B2 ligand or a tetrameric ephrin-B3 ligand. Furthermore, the composition of this invention can be a tetrameric EphB1 receptor/tetrameric ephrin-B1 ligand complex, a tetrameric EphB2 receptor/ephrin-B2 ligand complex, a tetrameric EphB3 receptor/ephrin-B3 ligand complex, or a tetrameric EphB receptor/ephrin-B ligand complex having any combination of EphB receptor and ephrin-B ligand.

The production of such multimeric Eph receptor ligands or multimeric Eph receptors can be carried out by methods known in the art and as provided herein for producing a multimeric Eph receptor binding ligand having more than two ligand subunits or a multimeric Eph receptor having more than two receptor subunits. For example, for the production of multimeric Eph receptor ligands, proteins are engineered in a two step approach to permit defined oligomerization. A number of natural examples exist for interaction "cassettes" to be incorporate in tandem arrangements in multidomain proteins. For the most part, these serve as adapter molecules that serve as scaffolds to associate different proteins to accomplish complex sequential reactions. This tandem adapter function is exploited to generate a series of adapter proteins that serve as binding scaffolds. Protein ligands are expressed as recombinant proteins containing the ectodomain linked to a high affinity epitope recognition binding site for the adapter domain to create a fusion protein ligand monomer. Adapter proteins are engineered to contain, in tandem, multiple defined copies (1,2, 4,6) of a selected interaction motif (e.g., SH2, SH3, PDB, PDZ, etc.). Adapter proteins and epitope tagged ligand recombinant proteins are expressed independently, in bacterial expression systems (adapter) or eukaryotic cell (CHO or sf9 insect cells) expression systems (ephrin ectodomain-tag). The epitope tagged ephrin ectodomains are expressed as secreted fusion proteins containing the recognition motif for the adapter cassette on the C-terminus, analogous to the position of the current ectodomain fusions. In cases where SH2 or PDB domains have been used, the recombinant ligand-epitope fusion will require tyrosine phosphorylation of the epitope to create the high affinity binding site.

These recombinant proteins are mixed in defined ratios and subsequently characterized as described in the Examples provided herein to determine the oligomeric state of the respective ligands. This approach permits strict definition of the ligand oligomers and provides a method for rigorously evaluating biological functions, as agonists and antagonists for specific receptor and their associated activities. Additional motifs may be engineered on either N or C termini to facilitate attachment of these adapter proteins to solid phase surfaces, for both purification and for solid phase attachment (e.g., for endothelialization of a prosthesis).

The multimeric ligands of this invention can be multimers of ephrin-A 1, ephrin-A2, ephrin-A3, ephrin-A4, ephrin-A5, ephrin-B1, ephrin-B2 and ephrin-B3, as well as any other ligand now known or identified in the future to promote the activities of this invention when in multimeric (e.g., tetrameric) form. Thus, the present invention provides tetrameric ephrin-A1, tetrameric ephrin-A2, tetrameric ephrin-A3, tetrameric ephrin-A4, tetrameric ephrin-A5, tetrameric ephrin-B1, tetrameric ephrin-B2 and tetrameric ephrin-B3.

Further provided in the present invention is an isolated multimeric Eph receptor. The receptor can be isolated and purified, if desired, according to standard protein isolation and/or purification protocols well known in the art. The multimeric receptor of this invention can be, but is not limited to multimers of EphA1, EphA2, EphA3, EphA4, EphA5, EphA6, EphA7, EphA8, EphB1, EphB2, EphB3, EphB4 and EphB5, as well as any other receptor now known or identified in the future to promote the activities of this invention when in multimeric (e.g. tetrameric) form. Thus, the present invention provides tetrameric EphA1, tetrameric EphA2, tetrameric EphA3, tetrameric EphA4, tetrameric EphA5, tetrameric EphA6, tetrameric EphA7, tetrameric EphA8, tetrameric EphB1, tetrameric EphB2, tetrameric EphB3, tetrameric EphB4 and tetrameric EphB5.

The present invention also provides a method for screening Eph receptor binding ligands for the ability to promote cell attachment when in multimeric form, comprising: producing a multimeric Eph receptor binding ligand; contacting the multimeric ligand with cells which express Eph receptors; and determining an amount of cell attachment and migration in the presence of the multimeric ligand as compared to the amount of cell attachment and migration without the multimeric ligand, whereby an increase in cell attachment and migration in cells contacted with the multimeric ligand as compared with the amount of cell attachment and migration in cells not contacted with the multimeric ligand identifies an Eph receptor binding ligand having the ability to promote cell attachment and migration when in multimeric form.

Additionally provided is a method for screening Eph receptor binding ligands for the ability to promote cell-cell assembly when in multimeric form, comprising: producing a multimeric Eph receptor binding ligand; contacting the multimeric ligand with cells which express Eph receptors; and determining an amount of cell-cell assembly in the presence of the multimeric ligand as compared to the amount of cell-cell assembly without the multimeric ligand, whereby an increase in cell to cell assembly of cells contacted with the multimeric ligand as compared with the amount of cell to cell assembly in cells not contacted with the multimeric ligand identifies a ligand having the ability to promote cell to cell assembly when in multimeric form.

A method is also provided herein for screening Eph receptor binding ligands for the ability to promote cell migration and/or expression of surface molecules affecting leukocyte attachment and migration when in multimeric form, comprising: producing a multimeric Eph receptor binding ligand; contacting the multimeric ligand with cells which express Eph receptors; and determining an amount of migration and/or expression of surface molecules affecting leukocyte attachment and migration in the presence of the multimeric ligand as compared to the amount of migration and/or expression of surface molecules affecting leukocyte attachment and migration without the multimeric ligand, whereby an increase in the amount of migration and/or expression of surface molecules affecting leukocyte attachment and migration in the presence of the multimeric ligand as compared to the amount in the absence of the multimeric ligand indicates an Eph receptor binding ligand having the ability to promote migration and/or expression of surface molecules affecting leukocyte attachment and migration when in multimeric form.

Further provided is a method for screening Eph receptor binding ligands for the ability to initiate, promote and direct neural cell migration and repair when in multimeric form, comprising: producing a multimeric Eph receptor binding ligand; contacting the multimeric ligand with neural cells which express Eph receptors; and determining an amount of neural cell migration and repair in the presence of the multimeric ligand as compared to the amount of neural cell migration and repair without the multimeric ligand, whereby an increase in the amount of neural cell migration and repair in the presence of the multimeric ligand as compared to the amount in the absence of the multimeric ligand indicates an Eph receptor binding ligand which can initiate, promote and direct neural cell migration and repair.

The present invention also provides a method for screening Eph receptors for the ability to promote cell attachment and/or when in multimeric form, comprising: producing a multimeric Eph receptor on the surface of cells which express Eph receptors; and determining an amount of cell attachment and/or migration in the presence of the multimeric receptor as compared to the amount of cell attachment and/or migration in cells without the multimeric receptor, whereby an increase in cell attachment and/or migration in cells with the multimeric receptor as compared with the amount of cell attachment and/or migration in cells not contacted with the multimeric receptor identifies an Eph receptor having the ability to promote cell attachment and/or migration when in multimeric form.

Additionally provided is a method for screening Eph receptors for the ability to promote cell-cell assembly when in multimeric form, comprising: producing a multimeric Eph receptor of the surface of cells which express Eph receptors; and determining an amount of cell-cell assembly in the presence of the multimeric receptor as compared to the amount of cell-cell assembly in cells without the multimeric receptor, whereby an increase in cell to cell assembly of cells with the multimeric receptor as compared with the amount of cell to cell assembly in cells without the multimeric receptor identifies a receptor having the ability to promote cell to cell assembly when in multimeric form.

A method is also provided herein for screening Eph receptors for the ability to promote migration and/or expression of surface molecules affecting leukocyte attachment and migration when in multimeric form, comprising: producing a multimeric Eph receptor on the surface of cells which express Eph receptors; and determining an amount of migration and/or expression of surface molecules affecting leukocyte attachment and migration in the presence of the multimeric receptor as compared to the amount of migration and/or expression of surface molecules affecting leukocyte attachment and migration without the multimeric receptor, whereby an increase in the amount of migration and/or expression of surface molecules affecting leukocyte attachment and migration in the presence of the multimeric receptor as compared to the amount in the absence of the multimeric receptor identifies an Eph receptor having the ability to promote migration and/or expression of surface molecules affecting leukocyte attachment and migration when in multimeric form.

Further provided is a method for screening Eph receptors for the ability to initiate, promote and direct neural cell migration and repair when in multimeric form, comprising: producing a multimeric Eph receptor on neural cells which express Eph receptors; and determining an amount of neural cell migration and repair in the presence of the multimeric receptor as compared to the amount of neural cell migration and repair without the multimeric receptor, whereby an increase in the amount of neural cell migration and repair in the presence of the multimeric receptor as compared to the amount in the absence of the multimeric receptor indicating an Eph receptor which can initiate, promote and direct neural cell migration and repair. The multimeric Eph receptor can be produced on the neural cells by inducing the formation of defined multimeric receptors according to the methods provided herein.

In another embodiment, the present invention provides a method for screening substances for the ability to inhibit the binding of a multimeric Eph receptor binding ligand to an Eph receptor comprising: contacting the substance with cells expressing an Eph receptor; contacting the cells with a multimeric Eph receptor binding ligand under conditions whereby the multimeric ligand can bind the receptor; and determining the activity induced by the cells contacted with the substance as compared to the activity of cells not contacted with the substance, whereby a reduction in activity of cells contacted with the substance as compared to the amount of activity of cells not contacted with the substance indicating a substance having the ability to inhibit the binding of a multimeric Eph receptor binding ligand to an Eph receptor.

In a specific embodiment, the present invention provides the following screening methods:

A. A method for screening an EphB receptor-binding ligand for the ability to initiate, promote and direct cell attachment to a matrix or to another cell when in multimeric form, comprising:
   a) contacting a multimeric EphB receptor-binding ligand with an EphB receptor-expressing cell under conditions whereby the ligand can bind the receptor; and
   b) detecting attachment of cells which have bound multimeric ligand as compared to attachment of cells which have not bound multimeric ligand, whereby attachment of cells which have bound multimeric ligand and no attachment of cells which have not bound multimeric ligand identifies an EphB receptor-binding ligand with the ability to initiate, promote and direct cell attachment to a matrix or to another cell when in multimeric form. Detection of cell attachment can be according to standard protocols known in the art and as set forth in the Examples provided herein. As used herein, no cell attachment means the absence of cell attachment or a lesser degree of cell attachment in a control sample, relative to the detection of attachment in the experimental sample.

B. A method for screening an EphB receptor-binding ligand for the ability to promote cell migration when in multimeric form, comprising:
   a) contacting a multimeric EphB receptor-binding ligand with an EphB receptor-expressing cell under conditions whereby the ligand can bind the receptor; and
   b) detecting migration of cells which have bound multimeric ligand as compared to migration of cells which have not bound multimeric ligand, whereby migration of cells which have bound multimeric ligand and no migration of cells which have not bound multimeric ligand identifies an EphB receptor-binding ligand with the ability to promote cell migration when in multimeric form. Detection of cell migration can be according to methods well known in the art and as set forth in the Examples provided herein. As used herein, no migration means the absence of migration or a lesser amount of migration in a control sample, relative to the detection of cell migration in an experimental sample.

C. A method for screening an EphB receptor-binding ligand for the ability to promote expression of a molecule on the surface of an EphB receptor-expressing cell, wherein the expressed molecule affects leukocyte or platelet attachment and migration, when in multimeric form, comprising:
   a) contacting a multimeric EphB receptor-binding ligand with a cell which expresses an EphB receptor under conditions whereby the ligand can bind the receptor; and
   b) detecting expression of a molecule which affects leukocyte or platelet attachment and migration on the surface of cells which have bound multimeric ligand as compared to expression of a molecule which affects leukocyte or platelet attachment and migration on the surface of cells which have not bound multimeric ligand, whereby expression of a molecule which affects leukocyte or platelet attachment and migration on the surface of cells which have bound multimeric ligand and no expression of a molecule which affects leukocyte or platelet attachment and migration on the surface of cells which have not bound multimeric ligand identifies a ligand with the ability to promote the expression of a molecule which affects leukocyte or platelet attachment and migration on the surface of cells, when the ligand is in multimeric form. The expression of a molecule of this invention can be detected according to methods well known in the art and as set forth in the Examples provided herein. As used herein, no expression means the absence of expression or a lesser amount of expression detected in a control sample, relative to the detection of expression in an experimental sample.

D. A method for screening an EphB receptor-binding ligand for the ability to promote function of a molecule on the surface of an EphB receptor-expressing cell, wherein the function of the molecule affects leukocyte or platelet attachment and migration, when in multimeric form, comprising:
   a) contacting a multimeric EphB receptor-binding ligand with a cell which expresses an EphB receptor under conditions whereby the ligand can bind the receptor; and
   b) detecting function of a molecule which affects leukocyte or platelet attachment and migration on the surface of cells which have bound multimeric ligand as compared to function of a molecule which affects leukocyte or platelet attachment and migration on the surface of cells which have not bound multimeric ligand, whereby function of a molecule which affects leukocyte or platelet attachment and migration on the surface of cells which have bound multimeric ligand and no function of a molecule which affects leukocyte or platelet attachment and migration on the surface of cells which have not bound multimeric ligand identifies a ligand with the ability to promote function of a molecule which affects leukocyte or platelet attachment and migration on the surface of cells, when the ligand is in multimeric form. The detection of function of a molecule of this invention can be carried out by methods standard in the art and as set forth in the Examples provided herein. As used herein, no function means the absence of function or a lesser amount of function detected in a control sample, relative to detection of function of a molecule in an experimental sample.

E. A method for screening an EphB receptor-binding ligand for the ability to promote migration, survival or targeting of a neural cell when in multimeric form, comprising:
   a) contacting a multimeric EphB receptor-binding ligand with a neural cell which expresses an EphB receptor under conditions whereby the ligand can bind the receptor; and
   b) determining migration, survival or targeting of a neural cell which has bound multimeric ligand as compared to migration, survival or targeting of a neural cell which has not bound multimeric ligand, whereby migration, survival or targeting of a neural cell which has bound multimeric ligand and no migration, survival, or targeting of a neural cell which has not bound multimeric ligand identifies a ligand with the ability to promote migration, survival or targeting of a neural cell when in multimeric form.

Detection of migration, survival or targeting of a neural cell can be carried out according to methods standard in the art and as set forth in the Examples provided herein. As used herein, no migration, survival or targeting of a neural cell means absence of migration, survival or targeting or detection of a lesser amount of migration, survival, or targeting of a neural cell in a control sample, relative to detection of migration, survival or targeting of a neural cell in an experimental sample.

F. A method for screening an EphB receptor for the ability to initiate, promote and direct cell attachment to a matrix or to another cell when the receptor is in multimeric form, comprising:
  a) producing a multimeric EphB receptor on the surface of a cell which expresses an EphB receptor; and
  b) detecting attachment of cells with a multimeric EphB receptor as compared to attachment of cells without a multimeric EphB receptor, whereby attachment of cells with a multimeric EphB receptor and no attachment of cells without a multimeric EphB receptor identifies an EphB receptor with the ability to initiate, promote and direct cell attachment to a matrix or to another cell when in multimeric form. Detection of cell attachment can be according to standard protocols known in the art and as set forth in the Examples provided herein. As used herein, no cell attachment means the absence of cell attachment or a lesser degree of cell attachment in a control sample, relative to the detection of attachment in the experimental sample.

G. A method for screening an EphB receptor for the ability to promote cell migration when the receptor is in multimeric form, comprising:
  a) producing a multimeric EphB receptor on the surface of a cell which expresses an EphB receptor; and
  b) detecting migration of cells with a multimeric EphB receptor as compared to migration of cells without a multimeric EphB receptor, whereby migration of cells with a multimeric EphB receptor and no migration of cells without a multimeric EphB receptor identifies an EphB receptor with the ability to promote cell migration when in multimeric form. Detection of cell migration can be according to methods well known in the art and as set forth in the Examples provided herein. As used herein, no migration means the absence of migration or a lesser amount of migration in a control sample, relative to the detection of cell migration in an experimental sample.

H. A method for screening an EphB receptor for the ability to promote expression of a molecule on the surface of an EphB receptor-expressing, wherein the expressed molecule affects leukocyte or platelet attachment and migration, when the receptor is in multimeric form, comprising:
  a) producing a multimeric EphB receptor on the surface of a cell which expresses an EphB receptor; and
  b) detecting expression of a molecule which affects leukocyte or platelet attachment and migration on the surface of cells with a multimeric EphB receptor as compared to expression of a molecule which affects leukocyte or platelet attachment and migration on the surface of cells without a multimeric EphB receptor, whereby expression of a molecule which affects leukocyte or platelet attachment and migration on the surface of cells with a multimeric EphB receptor and no expression of a molecule which affects leukocyte or platelet attachment and migration on the surface of cells without a multimeric EphB receptor identifies an EphB receptor with the ability to promote expression of a molecule on the surface of a cell which expresses an EphB receptor, wherein the expressed molecule affects leukocyte or platelet attachment and migration, when the EphB receptor is in multimeric form. The expression of a molecule of this invention can be detected according to methods well known in the art and as set forth in the Examples provided herein. As used herein, no expression means the absence of expression or a lesser amount of expression detected in a control sample, relative to the detection of expression in an experimental sample.

I. A method for screening an EphB receptor for the ability to promote function of a molecule on the surface of an EphB receptor-expressing, wherein the function of the molecule affects leukocyte or platelet attachment and migration, when the receptor is in multimeric form, comprising:
  a) producing a multimeric EphB receptor on the surface of a cell which expresses an EphB receptor; and
  b) detecting function of a molecule which affects leukocyte or platelet attachment and migration on the surface of cells with a multimeric EphB receptor as compared to function of a molecule which affects leukocyte or platelet attachment and migration on the surface of cells without a multimeric EphB receptor, whereby function of a molecule which affects leukocyte or platelet attachment and migration on the surface of cells with a multimeric EphB receptor and no function of a molecule which affects leukocyte or platelet attachment and migration on the surface of cells without a multimeric EphB receptor identifies an EphB receptor with the ability to promote function of a molecule on the surface of a cell which expresses an EphB receptor, wherein the expressed molecule affects leukocyte or platelet attachment and migration, when the EphB receptor is in multimeric form. The detection of function of a molecule of this invention can be carried out by methods standard in the art and as set forth in the Examples provided herein. As used herein, no function means the absence of function or a lesser amount of function detected in a control sample, relative to detection of function of a molecule in an experimental sample.

J. A method for screening an EphB receptor for the ability to promote migration, survival or targeting of a neural cell when the receptor is in multimeric form, comprising:
  a) producing a multimeric EphB receptor on the surface of a neural cell which expresses an EphB receptor; and
  b) detecting migration, survival or targeting of neural cells with a multimeric EphB receptor as compared to migration, survival or targeting of neural cells without a multimeric EphB receptor, whereby migration survival or targeting of neural cells with a multimeric EphB receptor and no migration, survival or targeting of neural cells without a multimeric EphB receptor identifies an EphB receptor with the ability to promote migration, survival or targeting of neural cells when in multimeric form. Detection of migration, survival or targeting of a neural cell can be carried out according to methods standard in the art and as set forth in the Examples provided herein. As used herein, no migration, survival or targeting of a neural cell means absence of migration, survival or targeting or detection of a lesser amount of migration, survival, or targeting of a neural cell in a control sample, relative to detection of migration, survival or targeting of a neural cell in an experimental sample.

The activity induced by the binding of multimeric ligand to receptor on the cell surface can be tyrosine phosphorylation, cell proliferation, cell attachment, cell to cell assembly or any other activity as described in the examples provided herein. The conditions whereby the multimeric ligand can bind the receptor can be the conditions as set forth in the examples described herein, as well as any other conditions as would be able to be readily determined by an artisan, under which a receptor and ligand can bind one another and form a complex.

The present invention further provides a method for screening a substance for the ability to inhibit the binding of a multimeric EphB receptor-binding ligand to an EphB receptor comprising:

a) contacting the substance with a cell expressing an EphB receptor;

b) contacting the cell of step (a) with a multimeric EphB receptor-binding ligand under conditions whereby the multimeric ligand can bind the receptor; and c) detecting the binding of the multimeric ligand to the receptor, whereby no binding of the multimeric ligand to the receptor identifies a substance with the ability to inhibit the binding of a multimeric EphB receptor-binding ligand to an EphB receptor.

The detection of binding of the multimeric EphB receptor-binding ligand to the EphB receptor can be by detecting an activity such as cell attachment to a matrix or to another cell, cell migration, expression of a surface molecule affecting leukocyte or platelet attachment and migration, promotion of function of a surface molecule affecting leukocyte or platelet attachment and migration and promotion of migration, survival or targeting of a neural cell.

The inhibitory substance of this invention can be an antibody or other molecule or compound which binds the receptor or which binds the ligand, having the net effect of preventing formation of a multimeric ligand, preventing formation of a multimeric receptor or preventing binding of the ligand and receptor. Other substances can include proteins, peptides, or other molecules or compounds which interfere with the binding of ligand and receptor, either directly or indirectly. For example, the substance can be a monomeric or dimeric ligand or higher order multimeric ligand which has antagonistic activity, as well as other small molecules which interrupt the receptor interfaces that engage in multimer binding to activate Eph receptor in oligomeric forms that do not permit the signals evoked by ligand multimers to be generated (i.e., a pseudo-agonist effect). Additionally, the substance can be a ligand or receptor ectodomain which binds its respective target and occupies the necessary binding site, thereby inhibiting the binding of ligand and receptor.

The activity induced by the cells expressing an Eph receptor, upon contact with a multimeric Eph binding ligand can be, but is not limited to, cell attachment, cell-cell assembly, migration, expression of surface molecules affecting leukocyte attachment and migration, neural cell migration and repair and endothelial cell proliferation.

The present invention also provides a method for promoting angiogenesis, comprising contacting cells which are associated with angiogenesis with a substance which promotes multimerization of receptors associated with promoting angiogenesis. The substance can be a multimeric ligand, for example, a tetrameric ligand, which induces the formation of tetrameric receptors. The cells can be contacted with the substance either in vivo or ex vivo as described herein. Angiogenesis can also be promoted upon solid surfaces, as also described herein. The promotion of angiogenesis upon formation of multimeric receptors can be determined according to protocols well known in the art. An example of the promotion of angiogenesis in vivo with a multimeric receptor is described in the Examples herein.

In addition, the present invention provides a method for promoting angiogenesis comprising contacting cells having an Eph receptor with an Eph receptor binding ligand which promotes angiogenesis upon binding the Eph receptor of the cells. The promotion of angiogenesis can be at a vascular bed-specific site at which the promotion of angiogenic processes is desired because, for example, these processes have been interrupted due to a variety of conditions such as cancer, inflammatory arthritis and injury to endothelium due to conditions such as hypoxic injury, thermal injury, immunologic injury and toxic injury.

To target the promotion of angiogenesis to a vascular bed-specific site, cells can be engineered in vitro to express an Eph receptor which promotes angiogenesis upon binding an Eph receptor binding ligand, delivered to the site where promotion of angiogenesis is desired and contacted with the Eph receptor binding ligand to promote angiogenesis at the specific site. Cells could be delivered to the specific sites of interest by intravenous injection, local tissue infiltration or via a slow release implantable delivery system.

In addition, the present invention provides a method for disrupting and interrupting angiogenesis (i.e., promoting vascular regression) comprising contacting cells expressing an Eph receptor with a substance which inhibits binding of an Eph receptor binding ligand which promotes angiogenesis when bound to the Eph receptor expressed by the cells.

The angiogenesis to be targeted for disruption and interruption can be caused by such conditions as cancer, arthritis, proliferative retinopathy, ischemic tissue injury, reproductive activity (e.g., ovulation and menstruation) and any other condition associated with angiogenesis. Furthermore, the angiogenesis can be targeted for disruption and interruption at a specific site in a subject, such as, for example, a tumor, the retina, an inflammatory condition and any site of vascular malformation.

The substance which disrupts and/or interrupts angiogenesis by inhibiting binding of an Eph receptor binding ligand which promotes angiogenesis when bound to Eph receptor can be antibodies which bind the ligand, thereby inhibiting binding of the ligand to the receptor, or antibodies which bind the receptor, thereby inhibiting binding of the ligand to the receptor. Additional substances applicable for this method of inhibiting angiogenesis can include proteins, peptides, or other molecules which interfere with the binding of ligand and receptor, either directly or indirectly. For example, the substance can be a dimeric ligand which has antagonistic activity, as well as other small molecules which interrupt the receptor interfaces that engage in multimer binding to activate Eph receptor in oligomeric forms that do not permit the signals evoked by ligand multimers to be generated (i.e., a pseudo-agonist effect). Additionally, the substance can be a ligand or receptor ectodomain which binds its respective target and occupies the necessary binding site, thereby inhibiting the binding of ligand and receptor.

Also contemplated in the present invention is a method for treating a disease associated with pathological angiogenesis in a subject comprising contacting cells of the subject, which are undergoing pathological angiogenesis and which have an Eph receptor, with a substance which inhibits binding of an Eph receptor binding ligand which promotes angiogenesis upon binding the Eph receptor. The substance can be an antibody which binds the Eph receptor and inhibits ligand binding to the receptor or an antibody which binds the Eph receptor binding ligand and inhibits ligand binding. Additional substances applicable for this method of inhibiting angiogenesis can include proteins, peptides, or other molecules which interfere with the binding of ligand and receptor, either directly or indirectly. For example, the substance can be a dimeric ligand which has antagonistic activity, as well as other small molecules which interrupt the receptor interfaces that engage in multimer binding to activate Eph receptor in oligomeric forms that do not permit the signals evoked by ligand multimers to be generated (i.e., a pseudo-agonist effect). Additionally, the substance can be a ligand or receptor ectodomain which binds its respective target and occupies the necessary binding site, thereby inhibiting the binding of ligand and receptor.

The disease associated with pathological angiogenesis can be a variety of conditions, such as cancer, destructive arthritis and proliferative retinopathy.

A method is also provided for treating a condition associated with interruption of angiogenic processes in a subject, such as cancer, inflammatory arthritis and the like, comprising contacting cells of the subject, which are involved with the interruption of angiogenic processes and which have an Eph receptor, with an Eph receptor binding ligand which promotes angiogenesis upon binding the Eph receptor of the cells.

In particular, the present invention provides the following methods:

K. A method for promoting angiogenesis, comprising contacting EphB receptor-expressing cells which are associated with angiogenesis with a multimeric EphB receptor-binding ligand, whereby binding of the tetrameric ligand promotes multimerization of the EphB receptor, thereby promoting angiogenesis.

L. A method for disrupting angiogenesis comprising contacting an EphB receptor-expressing cell which promotes angiogenesis upon binding a multimeric EphB receptor-binding ligand with a substance which prevents formation of a multimeric EphB receptor-binding ligand or inhibits binding of the multimeric EphB receptor-binding ligand to the receptor, thereby disrupting angiogenesis.

M. A method for treating a disease associated with pathological angiogenesis in a subject, comprising contacting an EphB receptor-expressing cell of the subject which promotes angiogenesis upon binding a tetrameric EphB receptor-binding ligand with a substance which prevents binding of the tetrameric ligand, thereby disrupting angiogenesis and treating a disease associated with pathological angiogenesis.

N. A method for treating a condition associated with interruption of angiogenic processes in a subject, comprising contacting an EphB receptor-expressing cell of the subject with a tetrameric EphB receptor-binding ligand, whereby binding of the tetrameric ligand promotes multimerization of the EphB receptor, thereby promoting angiogenesis and treating a condition associated with interruption of angiogenic processes.

Furthermore, the present invention provides a method for screening a substance for the ability to inhibit angiogenesis comprising: contacting the substance with cells having an Eph receptor; contacting the cells with an Eph receptor binding ligand which promotes angiogenesis upon binding the Eph receptor of the cells, under conditions whereby the ligand can bind the cell receptor; and detecting an amount of angiogenesis in cells contacted with the substance and the ligand as compared to the amount of angiogenesis in cells not contacted with the substance and contacted with the ligand, whereby a decrease in the amount of angiogenesis in cells contacted with the substance as compared to the amount of angiogenesis in cells not contacted with the substance identifying a substance having the ability to inhibit angiogenesis.

Specifically provided is a method for screening a substance for the ability to inhibit angiogenesis, comprising:

a) contacting the substance with a cell expressing an EphB receptor;

b) contacting the cell of step (a) with a multimeric EphB receptor-binding ligand, which promotes angiogenesis, under conditions whereby the multimeric ligand can bind the receptor; and c) detecting angiogenesis in cells contacted with the substance, as compared to angiogenesis in cells not contacted with the substance, whereby no angiogenesis in cells contacted with the substance and angiogenesis in cells not contacted with the substance identifies a substance having the ability to inhibit angiogenesis.

Further provided is a method for screening Eph receptor binding ligands for the ability to promote angiogenesis, comprising: contacting an Eph receptor binding ligand with cells having an Eph receptor; and detecting angiogenesis in the cells contacted with the ligand as compared to angiogenesis in cells not contacted with the ligand.

Also specifically provided is a method for screening an EphB-receptor binding ligand for the ability to promote angiogenesis when in multimeric form, comprising:

a) contacting a multimeric EphB receptor-binding ligand with a cell which expresses an EphB receptor under conditions whereby the ligand can bind the receptor; and b) detecting angiogenesis of cells which have bound multimeric ligand as compared to angiogenesis of cells which have not bound multimeric ligand, whereby angiogenesis of cells which have bound multimeric ligand and no angiogenesis of cells which have not bound multimeric ligand identifies an EphB receptor-binding ligand with the ability to promote angiogenesis when in multimeric form.

The cells which can be used in the screening methods of this invention can include endothelial cells and derived cell lines with origin in any human or animal vascular bed. For example, the cells can express the ephrin A1 receptor and be contacted with the Eph-A2 ligand.

The angiogenesis of the screening methods of this invention can be detected with a variety of experimental systems, including but not limited to, corneal pocket assay (44), chick chorioallantoic membrane assay (43), hamster skin flap windows, in vitro endothelial assembly (e.g. by detection of migration, cell attachment, cell to cell assembly, etc.) and Matrigel injection into animal tissues.

The following examples are intended to illustrate, but not limit, the invention. While the protocols described are typical of those that might be used, other procedures known to those skilled in the art may be alternatively employed.

EXAMPLES

Example 1

Eph Receptors Discriminate Specific Ligand Oligomers to Determine Alternative Signaling Complexes, Attachment and Assembly Responses Reagents. Anti-EphB1 (15) and anti-EphB2 (28) sera were described previously. Monoclonal phosphotyrosine antibody (4G10) was from Upstate Biotechnology Inc., Lake Placid, N.Y. Monoclonal anti-human IgG1 (anti-Fc) antibody was from The Binding Site, Birmingham, United Kingdom. Polyclonal rabbit antiserum to LMW-PTP was generated against the entire coding region (11) and affinity purified by adsorption and elution, using 2M glycine pH2.5, from recombinant LMW-PTP protein immobilized on Immobilin P membranes.

Ligand stimulation and immunoprecipitation of endogenous EphB receptors. Primary HRMEC were used at passages 3–6, as described (12). P19 cells were cultured as recommended (ATCC, Rockville, Md.). Ninety min prior to ligand stimulation, cells ($2 \times 10^5$ cells/60 mm dish) were plated on Matrigel- (Collaborative Biomedical Products, Becton Dickinson, Bedford, Mass., as recommended) or fibronectin-coated (29) dishes. Ligand (ephrin-B1/Fc) or control (ORF/Fc) (30) multimers were generated by preincubation with anti-Fc at a fixed ratio of 0.1× the indicated concentrations of Fc fusion proteins [50 ng ml$^{-1}$ anti-Fc for 500 ng ml$^{-1}$ Fc fusion protein]. If not otherwise indicated, Fc fusion proteins (ephrinB1/Fc or ORF/Fc) were used at 500 ng ml$^{-1}$ in the absence or presence of preclustering anti-Fc at 50 ng ml$^{-1}$. Cells were incubated with agonists at 37° C. for 10 min, or as described in the figure legends. Immunoprecipitations were conducted on either cell lysates (P19) or on *Triticum vulgaris* lectin affinity purified fractions of HRMEC (15) (needed to reduce the background from Matrigel). Precipitated proteins were analyzed by immunoblot (15).

Endothelial assembly into capillary-like structures. Twelve well plates (Falcon) were coated with thin layers of Matrigel. HRMEC were plated at a density of $4 \times 10^4$ cells/well in DME containing 1% fetal bovine serum. Indicated agonists, control peptides, alone, or in combination with the EphB1/Fc antagonist (1000 ng ml$^{-1}$) (FIG. 5) were added at the time of plating. Cells were incubated at 37° C. for 8 h and photographed using phase microscopy (magnification 100×) (Diaphot-TMD, Nikon).

Cell adhesion assay. Six well plates (Falcon) were coated with thin layers of Matrigel or with 0.5 $\mu$g cm$^2$ fibronectin (29). Growth medium was replaced 48 h before harvest with binding medium, either DMEM (HRMEC) or -MEM (P19) containing 1% bovine albumin. Cells were recovered by trypsinization (HRMEC) or vigorous tituration (P19) and washed three times with binding medium and plated at $1 \times 10^5$ cells per well. Ligands were added coincident with plating at concentrations indicated above. After 90 min, unattached cells were dislodged by applying 4 brisk slaps of the plate on a horizontal surface, and the attached cell layer was carefully washed once with PBS containing calcium and magnesium to collect the remaining unattached cells. Attached cells were collected after incubation in Dispase (Collaborative Biomedical Products). Separate fractions were recovered by centrifugation, washed once and trypan blue excluding cells counted visually using a hemocytomer. The ratio of attached to total number of cells recovered were calculated for each of three wells. Data are expressed as mean +/–SEM and are representative of three independent experiments.

Transfections. P19 cells were transfected with a total of 10 $\mu$g plasmid DNA per P100 plate using the Lipofectamine method (Gibco/BRL). As indicated, pSR -EphB1/HA or pSR -EphB1-Y929F/HA were mixed prior to transfection at the ratio indicated in FIG. 4. Forty h after transfection, cells from the same transfections were used in attachment assays and in immunoprecipitation experiments. Displayed data represent those from 3 independent experiments.

GST-EphB1 affinity binding assays. Recombinant GST-EphB I1cy and GST-EphB1-Y929F/HA proteins were expressed in Sf9 cells as described (15), premixed in defined ratios where indicated, bound to glutathione-sepharose, kinased and used as an affinity matrix to evaluate LMW-PTP binding, as described in the figure legend.

Eph family receptor tyrosine kinases (including EphA3, EphB4) direct pathfinding of neurons within migratory fields of cells expressing gradients of their membrane-bound ligands, ephrins (ephrin-A2,ephrin-B2) (1–6). EphB1 and EphA2 direct vascular network assembly, affecting endothelial migration, capillary morphogenesis and angiogenesis (7,8). To explore how ephrins could provide positional labels for cell targeting, EphB1 (ELK) and EphB2 (Nuk) receptors were tested to determine whether they discriminate between variably oligomerized forms of an ephrin-B1/Fc fusion ligand (9,10) presented to P19 and endothelial cells.

To test if variably oligomerized forms of ephrin-B1 evoke alternative signals through EphB receptors, a disulfide-linked immunoglobulin Fc fusion form of ephrin-B1 (ephrin-B1/Fc) (9) was used. Ephrin-B1/Fc dimers, or anti-Fc clustered multimers were presented to each of two cell types that express endogenous EphB1 receptors, human renal microvascular endothelial cells (HRMEC) (12) and teratocarcinoma-derived, pluripotent murine cells, P19 (13) (ATCC accession number CRL 1825). As shown in FIG. 1A, both dimeric and multimeric forms of ephrin-B1/Fc promoted endothelial EphB1 activation and tyrosine phosphorylation at concentrations from 15–1000 ng ml$^{-1}$.

Figure 1B:
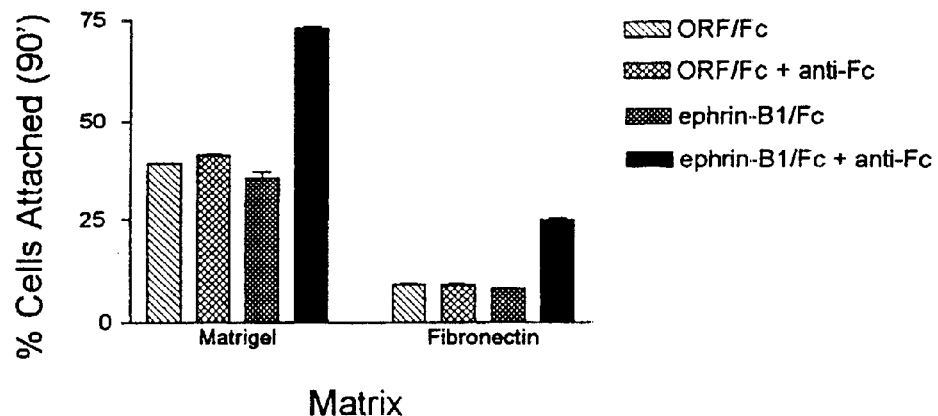

However, in sharp contrast to this observation, marked differences in cellular behavior were observed (FIG. 1A). Preclustered, multimeric ephrin-B1/Fc promoted endothelial capillary-like assembly in a two dimensional in vitro assay (12), while dimeric ephrin-B1/Fc did not, at concentrations that stimulated receptor tyrosine phosphorylation. Dimeric and preclustered multimeric forms of an irrelevant open reading frame Fc fusion protein (ORF/Fc) were inactive at these concentrations (FIG. 1A). In a second assay, ephrin-B1/Fc multimers promoted HRMEC attachment to Matrigel- and fibronectin-coated surfaces, while dimers did not (FIG. 1B).

Figure 1C:
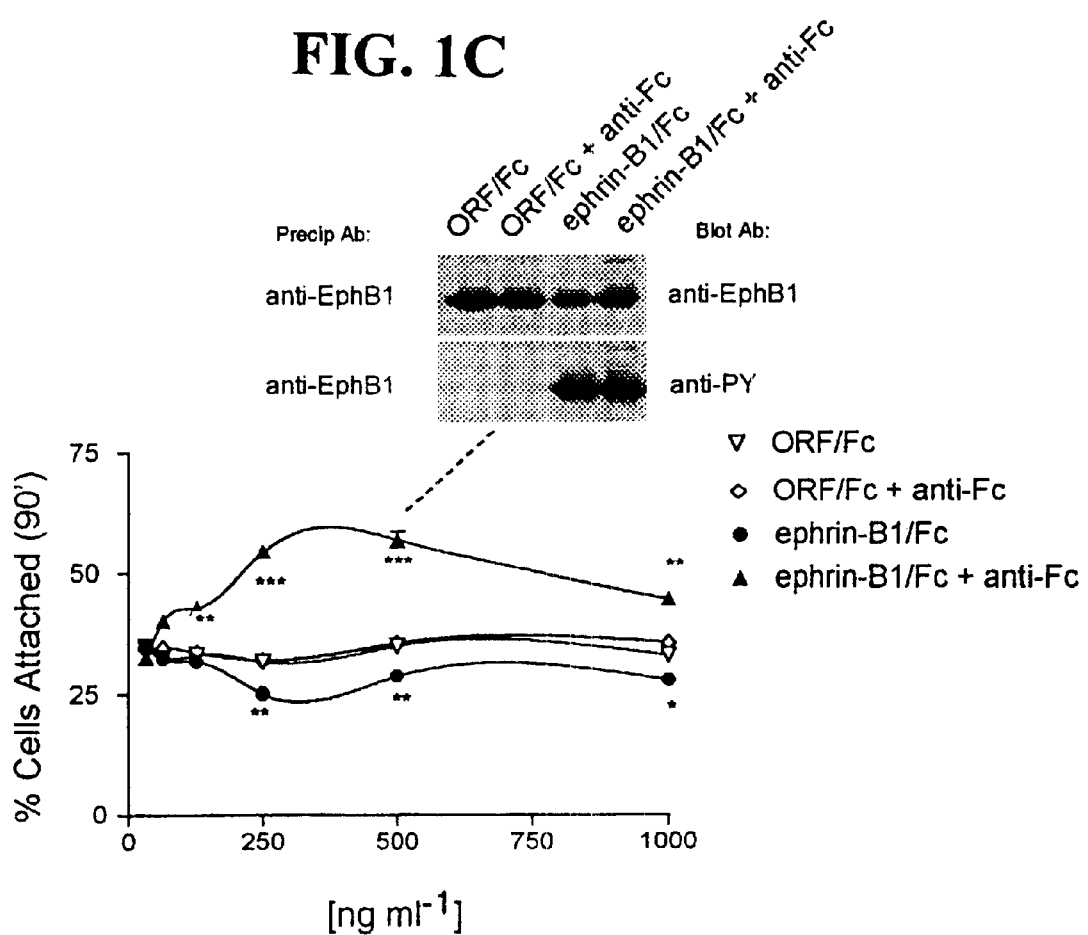

Differential responses were also noted in P19 cells (FIG. 1C). Preclustered ephrin-B1/Fc multimers promoted P19 attachment to fibronectin, while ephrin-B1/Fc dimers had a modest effect to decrease fibronectin attachment of a small subpopulation of cells, notably at concentrations where multimers increased attachment. Thus, two different cell types show specific attachment and assembly responses that depend upon the oligomeric form of ephrin-B1/Fc presented.

Given that other EphB subclass receptors share a similar affinity for ephrin-B1 (14), ephrin-B1 dimers and multimers were evaluated to determine whether they could variably activate or recruit other EphB subclass receptors (14). HRMEC were screened for EphB2, EphB3 and EphB4 mRNA using specific primers and RT-PCR. Among these, only EphB2 was expressed at detectable levels.

EphB1 and EphB2 immunoprecipitates from HRMEC stimulated with dimeric or multimeric (+anti-Fc) ephrin-B1/Fc were analyzed for receptor activation (anti-PY), and coprecipitation of heteromeric receptors (anti-EphB1, or anti-EphB2). Coprecipitating proteins were identified by immunoblots, using anti-pTyr, anti-EphB2 and anti-EphB1 antibodies, of EphB1 receptor immunoprecipitates from HRMEC or P19 cells and EphB2 receptor immunoprecipitates (from HRMEC) from cells exposed to no addition, or Fc fusion proteins (500 ng ml$^{-1}$), ORF/Fc or EphB1/Fc, in either dimeric (–anti-Fc) or multimeric (+anti-Fc) forms.

These studies demonstrated that ephrin-B1/Fc dimers or preclustered multimers (+anti-Fc) stimulated tyrosine phosphorylation of EphB2, similar to that seen with EphB1. Immunoprecipitation of either EphB1 or EphB2 failed to recover the other receptor, or the activating ephrin-B1/Fc, in a stable complex following activation. Although more than one EphB subclass receptor was activated, each receptor (EphB1 and EphB2) was similarly activated by ephrin-B1 dimers and multimers.

It was reasoned that alternative signaling responses mediated through EphB receptors might reflect differential association of additional receptor signaling complex components. Recruitment of SH2-containing adapter proteins, Grb2 and Grb10 (15) and Nck to EphB1 complexes did not differ between dimeric and multimeric ephrin-B1/Fc ligands. However, analysis of low molecular weight species recovered in EphB1 and EphB2 immunoprecipitates revealed an 18 kDa tyrosine phosphoprotein recruited by multimeric, but not by dimeric, ephrin-B1/Fc. A recent report demonstrated that the low molecular weight, human cytoplasmic phosphotyrosine phosphatase (LMW-PTP) is itself a substrate for v-src tyrosine phosphorylation (16). Accordingly, EphB1 immunoprecipitates were analyzed for LMW-PTP immunoreactivity (11,17). These studies demonstrated that affinity purified LMW-PTP antibodies recognized the 18 kDa tyrosine phosphoprotein in both EphB1 and EphB2 multimer-activated signaling complexes.

LMW-PTP is structurally distinct from the better studied tyrosine phosphatases (18), is expressed in a wide range of cell types, and structural homologues are expressed in yeast (19). A catalytically inactive LMW-PTP functions as a dominant negative protein that binds and precipitates tyrosine phosphorylated PDGF receptors and to promote cell proliferation (20). At least two alternatively spliced LMW-PTP isoforms exist. The A isoform (18) is the dominant species and it precipitates with EphB1 in response to multimeric, but not dimeric, ephrin-B1. EphB1 receptor tyrosine kinase phosphorylates LMW-PTP in vitro, and time courses have shown that LMW-PTP immunoreactivity is tyrosine phosphorylated as soon as it is detected in EphB1 complexes.

Whether LMW-PTP interacts directly with EphB1 was tested using yeast two hybrid and in vitro coprecipitation assays of recombinant proteins. Recombinant GST fusions containing EphB1 cytoplasmic domain (GST-EphB1cy), or a kinase-inactive mutant (GST-EphB1cyK652R), were immobilized on glutathione-sepharose, incubated in kinase buffer in the presence (+) or absence (−) of ATP (15), incubated with HRMEC extracts or recombinant LMW-PTP protein, washed extensively, then analyzed by immunoblot, using anti-GST and anti-LMW-PTP antibodies. Recombinant GST-EphB1cy and HA-epitope tagged GST-EphB1cy-Y929F were mixed in (%) ratios of 100:0, 75:25, 50:50, 25:75 and 0:100, bound to glutathione-sepharose and assayed as described herein. P19 cells were transfected with pSR expression constructs (27) encoding wild-type EphB1 (hEphB1/HA) or mutant (hEphB1-Y929F/HA) at (%) ratios of 100:0, 80:20, 60:40, 20:80 and 0:100, stimulated with precomplexed ephrin-B1/Fc, and assayed for either attachment, or LMW-PTP recruitment to anti-HA immunoprecipitated EphB1.

These experiments demonstrated that a recombinant GST-EphB1 cytoplasmic domain fusion protein (GST-EphB1$_{cy}$) binds purified recombinant LMW-PTP (A isoform) and endogenous LMW-PTP from crude endothelial cell lysates following self-phosphorylation in vitro. Kinase inactive (GST-EphB1$_{cy}$K652R) and unphosphorylated EphB1 cytoplasmic domains (GST-EphB1$_{cy}$, (−ATP) did not bind LMW-PTP. Yeast two hybrid interaction between LMW-PTP and EphB1$_{cy}$ required EphB1 residues 883–984, the carboxyterminal conserved sterile alpha motif shared by Eph family receptors (21). This domain includes a single tyrosine residue required for Grb10 binding (15). A site directed point mutation of this tyrosine residue (Y929F) disrupted LMW-PTP/EphB1$_{cy}$ interaction in two hybrid assays and in the recombinant protein interaction assay. Stoichiometric amounts of GST-EphB1$_{cy}$ (Y929F) blocked the capacity of GST-EphB1 to acquire LMW-PTP binding activity upon self-phosphorylation, providing strong evidence that Y929 is involved in the interaction, and suggesting that cooperative interaction between multiple EphB1$_{cy}$ subunits is required.

These findings led to an evaluation of the functional importance of LMW-PTP recruitment for the EphB1 mediated increases in P19 adhesion seen with multimeric ephrinB1/Fc. P19 cells were cotransfected with varying ratios of expression plasmids driving high level expression of epitope-tagged versions of EphB1, either wild type or (Y929F) mutant. Expression of increasing ratios of mutant (Y929F) receptor blocked both LMW-PTP recruitment to immunoprecipitated EphB1 complexes and the subsequent increases in attachment attending stimulation with multimeric ephrin-B1/Fc. This finding suggests that LMW-PTP may play a role in coupling receptor activation with attachment responses.

Figure 2A:
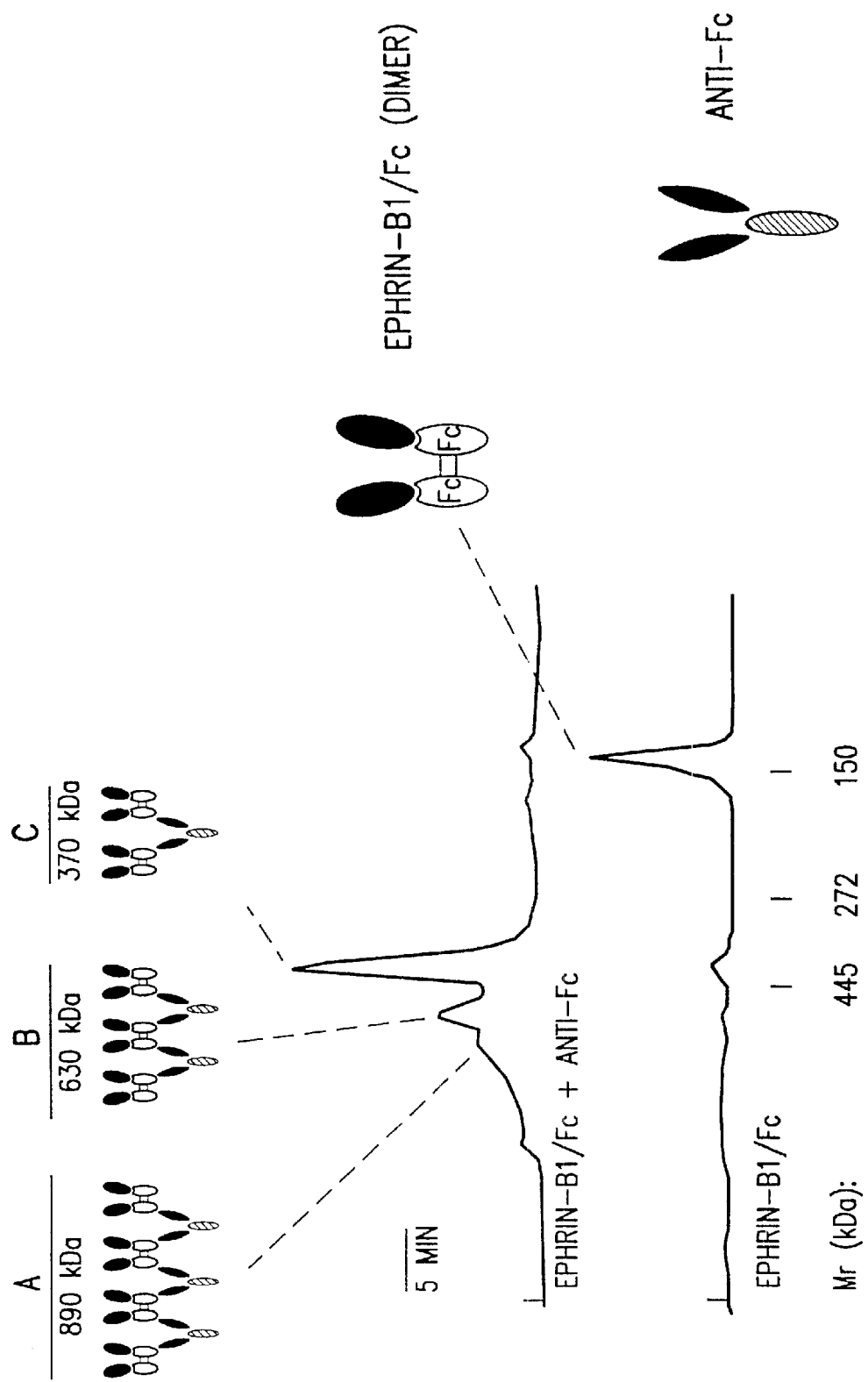
FIGS. 2A, 2B and 2C. Ephrin-B1/Fc tetramers recruit LMW-PTP to EphB1 and promote attachment.
Figure 2B:
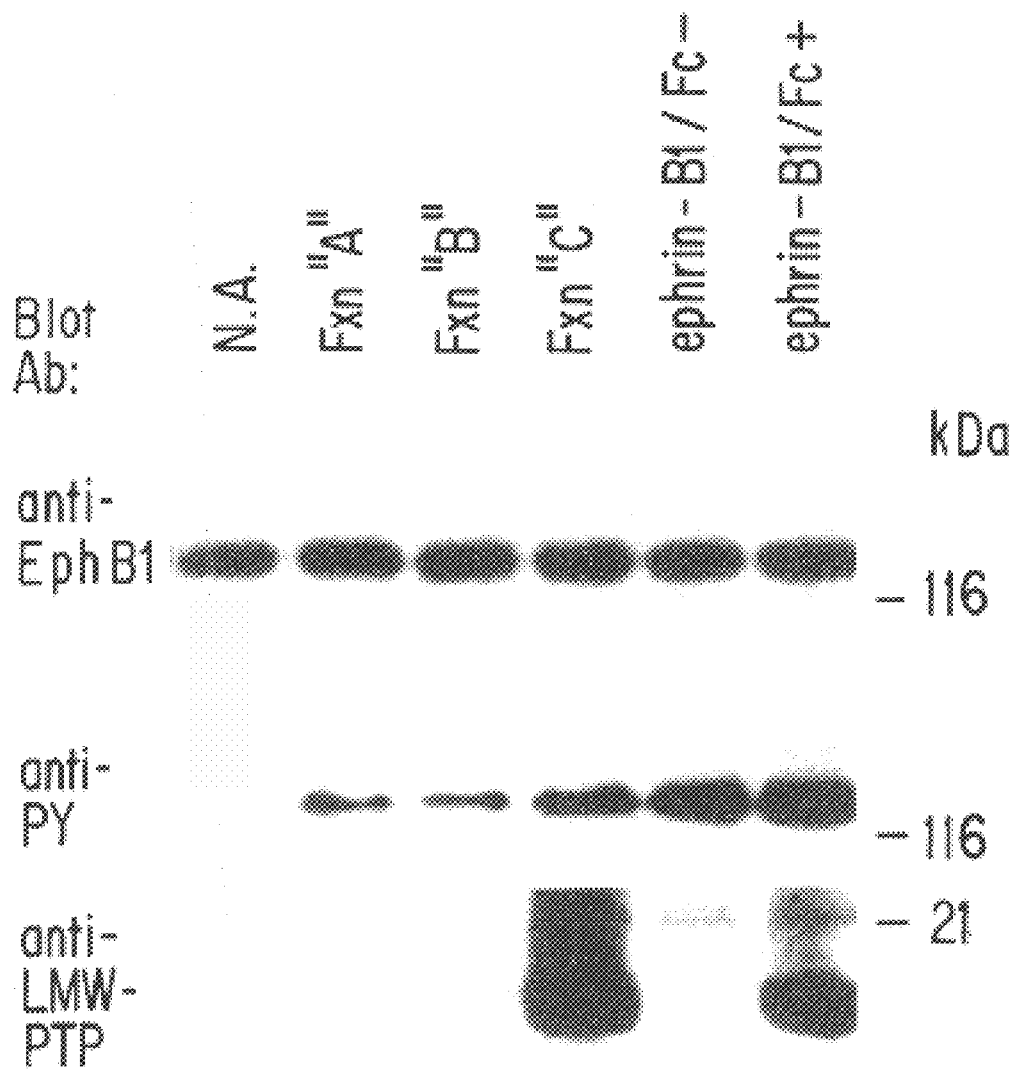
Figure 2C:
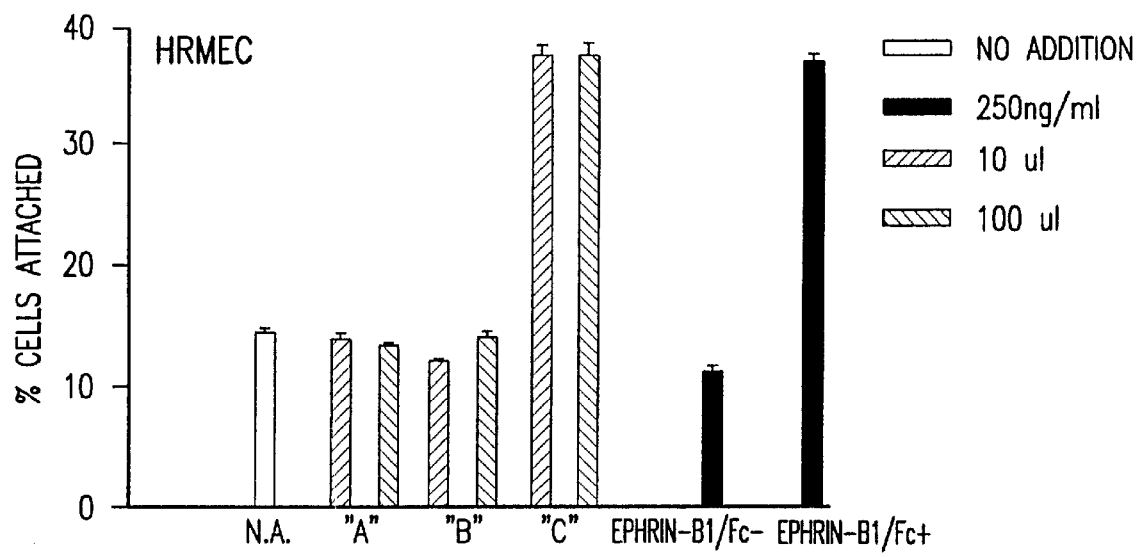
Figure 2C:
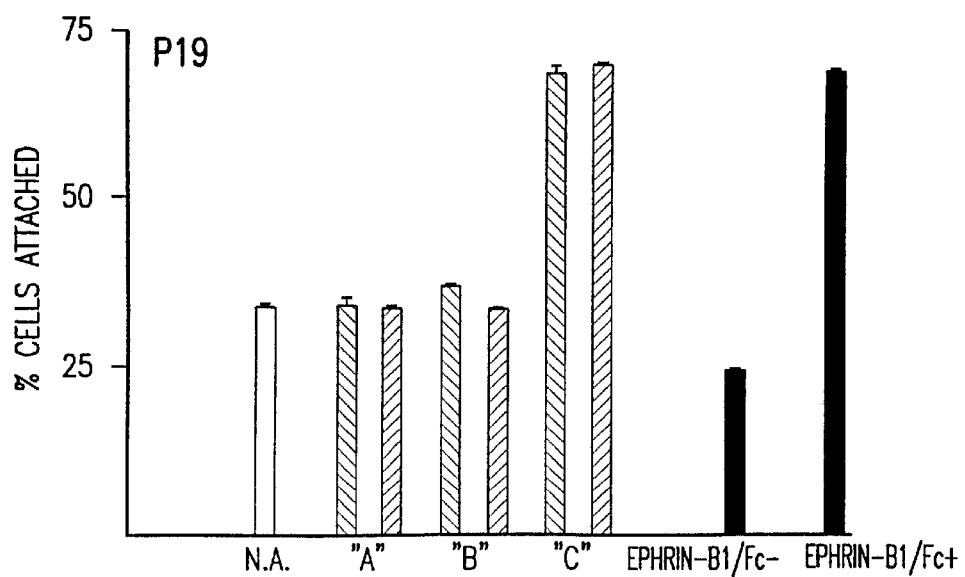

Because the ratio of preclustering monoclonal anti-Fc antibody to ephrin-B1/Fc was a critical determinant of cellular responses, studies were conducted to examine which ephrin-B1/Fc multimeric species determines recruitment of LMW-PTP to EphB1 and EphB2 complexes to promote cellular adhesion. Gel filtration chromatography separated 2 distinct peaks of size and composition consistent with ephrin-B1 tetramers and hexamers (Peaks "B" & "C"), as well as a broad peak containing higher order multimers (Peak "A") (FIG. 2A). Exposure of HRMEC and P19 cells to different dilutions of these fractions showed each was active to promote EphB1 receptor tyrosine phosphorylation, yet ephrin-B1/Fc multimers from fractions of peak "C" (complexes composed of two ephrin-B1/Fc dimers and one anti-Fc monoclonal antibody) uniquely promoted LMW-PTP recruitment (FIG. 2B) and increased adhesion (FIG. 2C).

In light of evidence that EphB3 is activated upon contact with ephrin-B1 expressing cells (22), and that HRMEC express ephrin-B1 and ephrin-B2 at high constitutive levels (8), the following were addressed: 1) whether EphB receptors are activated during endothelial capillary-like assembly, 2) whether this assembly is sensitive to inhibition of EphB1 engagement, and 3) whether the EphB1 complexes that form during juxtacrine activation include LMW-PTP.

HRMEC were plated in media supplemented with no addition (NA), PMA (20 ng ml$^{-1}$) or ephrinB1/Fc multimers (500 ng ml$^{-1}$+anti-Fc), in the absence or presence of the ectodomain competitor, EphB1/Fc (1000 ng ml$^{-1}$). Cells were harvested at 5 min (NA, ephrin-B1/Fc) or 100 min (PMA), and EphB1 or EphB2 complexes were analyzed by immunoblot, using anti-EphB2, anti-pTyr and anti-LMW-PTP antibodies. EphB1/Fc interrupts the EphB1 activation and LMW-PTP recruitment.

In a parallel experiment, HMREC were treated as above in the absence or presence of EphB1/Fc (1000 ng ml$^{-1}$), then photographed after 8 h. ELK/Fc interrupts the capillary-like assembly.

EphB1 and EphB2 are tyrosine phosphorylated and LMW-PTP is recruited during capillary-like endothelial assembly stimulated by the angiogenic agent, phorbol myristate acetate. EphB1 and EphB2 activation occurs through juxtacrine engagement, requiring that cells are plated at sufficient cell density to promote juxtacrine contact. Addition of exogenous receptor ectodomain, EphB1/Fc, at concentrations of 2–8 nM inhibited not only EphB1 and EphB2 tyrosine phosphorylation and LMW-PTP recruitment, but also capillary-like assembly. These findings argue strongly that native endothelial EphB1 and EphB2 ligands are presented to receptors through juxtacrine engagement to assemble receptor signaling complexes similar to those invoked by exogenous tetrameric ephrin-B1/Fc.

The specific response of EphB1 and EphB2 receptors to multimeric ephrinB1, to mediate assembly of alternative complexes and to promote cell attachment and cell-cell assembly, suggests that ligand oligomerization may be a control point involved in juxtacrine receptor responses required for cell targeting. Recent data demonstrated tyrosine phosphorylation of the ephrin-B1 cytoplasmic domain in response to engagement by NUK receptor ectodomain fusions (23,24), and ephrin-B1 has been implicated in developmental targeting of hippocampal neurons (25). These results suggested "outside-in" signaling through ephrin-B proteins. Alternatively, these data suggest that conserved cytoplasmic domain sequences among ephrin-B proteins (26) may participate in oligomerization of these "ligands" to provide positional labels and direct targeting of migrating vascular and neural cells as they assemble integrated networks. The surprising capacity of "activated" EphB receptors to direct alternative signaling events through discrete pathways uncovers an additional level of discrimination that is relevant for receptor tyrosine kinases that interact with soluble and membrane bound forms of ligand.

In summary, the studies described herein demonstrate that both dimeric and clustered tetrameric forms of ephrin-B1/Fc stimulated EphB1 & EphB2 activation (tyrosine phosphorylation), yet only ephrin-B1/Fc tetramers promoted cell attachment, capillary-like endothelial assembly and receptor recruitment of the low molecular weight phosphotyrosine phosphatase, LMW-PTP (11). The EphB1 binding site for LMW-PTP is required for downstream cell attachment responses. During capillary-like assembly, endogenous endothelial ephrins engaged EphB1 to recruit LMW-PTP, a process inhibited by an EphB1 ectodomain competitor (EphB1/Fc). EphB receptors signal different attachment and cell-cell assembly responses based upon their engagement of specific ephrin oligomers that may serve as positional labels to determine targeting.

A differential signaling effect of multimeric as compared with dimeric Ephrin-B1/Fc with regard to attachment responses to fibronectin-coated surfaces has also been demonstrated. Specifically, nitrocellulose coated surfaces were preadsorbed with 500 ng/well of non-denatured ephrin-B1/Fc, either as dimer (LERK-2/Fc) or preclustered multimer (LERK2/FC+anti-Fc) or control protein (anti-Fc, BSA), with fibronectin (500 ng/well). P19 cells were plated and the % attached cells were assayed after a 90 min incubation at 37° C.

These data showed approximately 40% attachment of cells in wells preadsorbed with ephrin-B1/Fc dimers as compared with approximately 60% attachment of cells in wells preadsorbed with ephrin-B1/Fc tetramers. These data demonstrate that Eph receptors are competent to engage ephrin-B1 displayed as an attached protein, as on a membrane. Furthermore, Eph discriminates the oligomeric state on a solid surface, similar to the manner in which it may be presented on cell surfaces through juxtacrine contact.

Vascular bed-specific promotion of angiogenesis with Eph ligands. On the basis of differential tissue distributions of Eph receptors and ligands, ephrin ligands from different classes (GPI-linked vs. transmembrane proteins) were examined for the ability to evoke different responses in endothelial cells derived from different vascular beds.

For these studies, HRMEC or HUVEC were plated on Matrigel-coated surfaces in defined medium in a two dimensional capillary-like assembly assay. Ephrin-B1 promoted capillary-like assembly of HRMEC, but not HUVEC, while ephrin-A1 promoted assembly of HUVEC but not HRMEC, in identical media at concentrations appropriate for their respective affinities for EphB1 and EphA. In each cell type, ephrin-B1 and ephrin-A1 promoted tyrosine phosphorylation of 130 kDa EphB1 and EphA2, both of which are expressed in each system. These findings show that endothelial cells cultured from different vascular beds are variably responsive to different ligands, despite similar capacity to activate receptors of both EphB and EphA subclasses.

The biological activity of multimeric ephrin-B1 has also been confirmed in an in vivo system. Specifically, tetramers of ephrin-B1 have been shown to promote angiogenesis in a chick chorioallantoic membrane (CAM) assay system as described by Folkman et al. (43) and in a mouse corneal model as described by Kenyon et al. (44) and the content of both of these references is incorporated in the entirety by reference herein.

Example 2

EphB Receptors Signal Activation of Cell-matrix Attachment through $\alpha_v\beta_3$ and $\alpha_5\beta_1$ Integrins Matrix proteins, peptides and antibodies. EphrinB1/Fc was provided by Immunex (Seattle, Wash.), monoclonal anti-human IgG1 (anti-Fc) was from the Binding Site (Birmingham, UK) and monoclonal anti-HA (12CA5) from Boehringer Mannheim (Indianapolis, Ind.) . Human IgG1 and plasma fibrinogen were from Sigma (St Louis, Mo.). Human plasma fibronectin and bovine serum albumin (BSA) were from Life Technologies (Gaithersburg, Md.). The GRGDTP (SEQ ID NO:1) and GRGESP (SEQ ID NO:2) peptides were from Calbiochem (La Jolla, Calif.), the GRGDSPK (SEQ ID NO:3) peptide from American Peptide Company (Sunnyvale, Calif.). The following anti-integrin blocking mAbs from Chemicon (Temecula, Calif.) were used: LM609 ($\alpha_v\beta_3$), P1F6 ($\alpha_5\beta_1$) JBS5 ($\alpha_v\beta_5$).

Cell culture and transfection. Human embryonic kidney cells, HEK293, were passaged in minimum essential medium (Life Technologies) supplemented with 10% fetal bovine serum (Hyclone Laboratories, Logan, Utah). HRMEC were cultured as described (12). HEK293 cells were transfected with Lipofectamine Plus (Life Technologies) as described by the manufacturer. The expression constructs pSRa-hEphB1-HA, pSRα-hEphB1-HA-K652R, pSRα-hEphB1-HA-Y596F and pSRα-hEphB1-HA-Y929F have been described previously (45,46). Cell attachment assays were performed 48 hours after transfection.

Solid phase cell attachment assays. Forty-eight-well plates (Falcon) were coated with a layer of nitrocellulose (Schleicher & Schuell) and allowed to air dry as described (47). Coated wells were incubated overnight at 4° C. with PBS containing matrix proteins at the indicated concentrations alone (no addition, NA) or in combination with dimeric EphrinB1/Fc. Two hours prior to assay, wells were washed twice then blocked at 37° C. with 1% BSA. Serum starved cells were harvested in 2 mM EDTA in PBS (HEK293) or recovered by trypsinization (HRMEC), washed twice in serum free medium containing 1% BSA, then plated at a density of $0.7–1\times10^5$ cells per well. After incubation at 37° C. for 1 hour (or as specified), unattached cells were dislodged by 5 brisk slaps of the plate on a horizontal surface. Wells were gently washed with PBS until cells were not adherent to albumin-coated wells. Adherent cells were fixed with 2% glutaraldehyde, stained with 0.5% crystal violet (in EtOH), and quantified by OD reading at 570 nm. In experiments using competitive peptides or blocking antibodies, cells were preincubated with the indicated peptides (100 μM) or antibodies (10 μg/ml) for 15 min at RT before plating. Results representative of three independent experiments are given as OD values and represent the mean of duplicate or triplicate wells±SEM.

In experiments to quantitate the mass of EphrinB 1/Fc adsorbed, 12-well plates were coated with nitrocellulose, fibrinogen and increasing amounts of EphrinB1/Fc (supplemented with biotin-conjugated EphrinB1/Fc at a molar ratio of 1:10) as described. After an overnight incubation at 4° C., supernatants were recovered, and wells were washed twice with PBS, prior to extraction of adsorbed proteins in boiling SDS-electrophoresis sample buffer. Biotinylated proteins in supernatant and adsorbed fractions were quantitated by comparison to standards of biotinylated ephrin-B1/Fc following electrophoresis and blotting using Streptavidin-HRP (Jackson, Westgrove, Pa.).

Surface biotinylation and integrin immunoprecipitation. To determine if surface integrin expression was altered by transfection and/or exposure to ephrinB1/Fc, cells were biotinylated for 30 min at 4° C. with 0.5 mg/ml Sulfo-NHS-LC-Biotin (Pierce, Rockford, Ill.) before plating onto 60 mm dishes coated with nitrocellulose, fibrinogen and EphrinB1/Fc. After a 60 min incubation at 37° C., cells were harvested in WG buffer (15) and immunoprecipitation performed with 2 ug of the integrin antibodies used in the competition experiments. After SDS-PAGE (non-reducing conditions) and Western blotting, biotinylated proteins were detected by enhanced chemiluminescence using ECL Western Blotting Detection (Amersham).

Figure 3B:
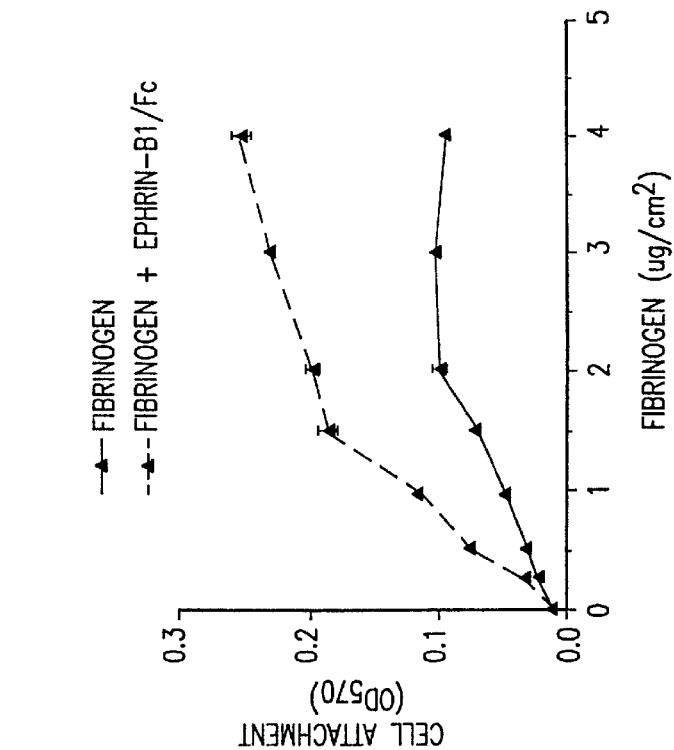
FIGS. 3A, 3B and 3C. Ephrin-B1/Fc adsorbed to nitrocellulose-coated surfaces stimulates $\alpha_v\beta_3$ integrin-mediated endothelial attachment at defined densities.
Figure 3A:
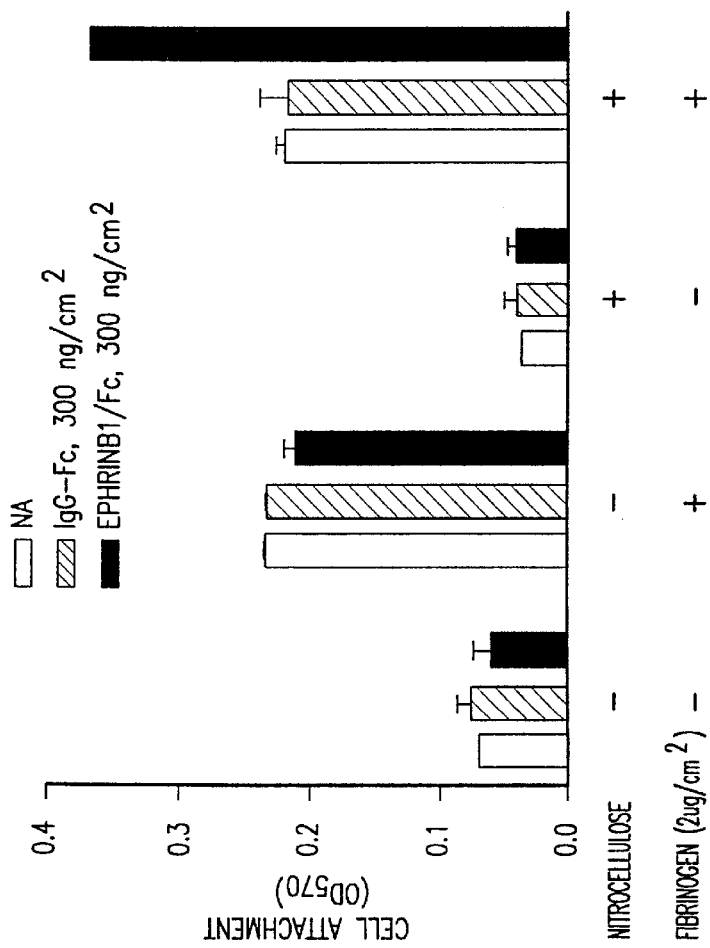
Figure 3C:
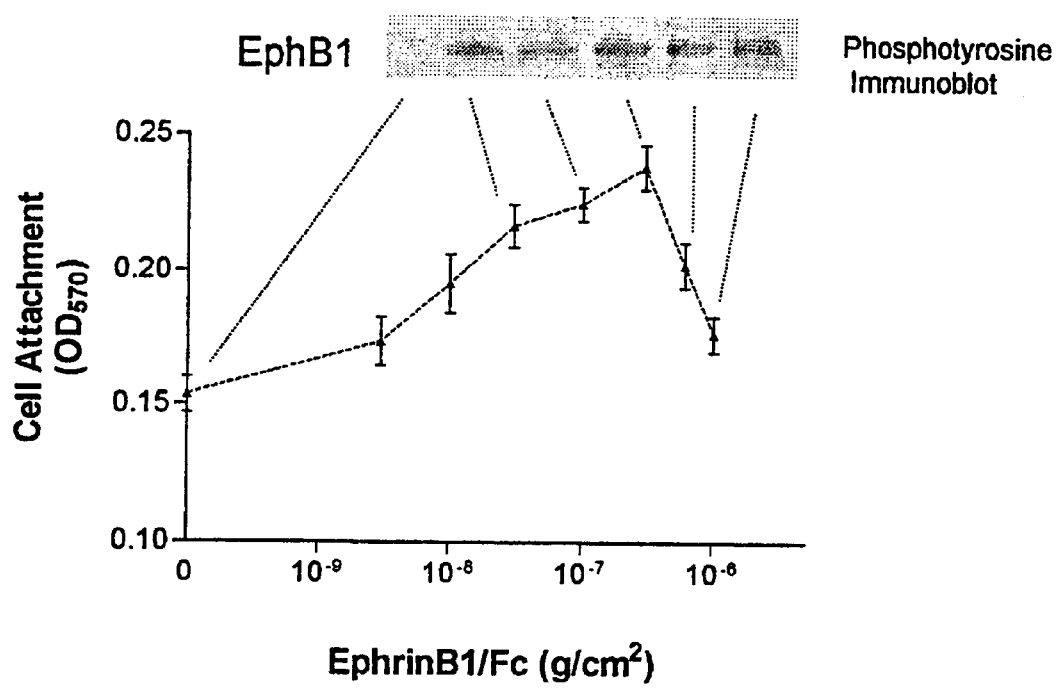

To reconstitute the surface display of ephrin-B1 in a native form similar to that encountered on membrane surfaces contacted by migratory cells and cell processes, the capacity of nitrocellulose to bind a recombinant fusion protein ligand, ephrin-B1/Fc, was exploited. As shown in FIG. 3A–3C, primary human renal microvascular endothelial cells that express endogenous EphB1 and EphB2 receptors (45) adhere poorly to plastic or nitrocellulose-coated plastic in serum-free medium, but attach effectively to fibrinogen-coated surfaces. Pre-coating of plates with ephrinB1/Fc, alone or in the presence of fibrinogen, using standard procedures, did not promote cell attachment. However, when adsorbed to nitrocellulose-coated surfaces under non-denaturing conditions, ephrin-B1/Fc was presented in a form that promoted endothelial attachment (FIG. 3A), compared with an Fc control, human $IgG_1$. This effect required that extracellular matrix components, either fibrinogen (FIG. 3B) or vitronectin (not shown), be adsorbed to the nitrocellulose surface, suggesting roles for integrins in the attachment. Although the surface density of adsorbed fibrinogen required to promote attachment showed a threshold at approximately 1 ug/cm², increasing fibrinogen surface density above that level showed modest impact on cell attachment in the absence of ephrin-B1.

In sharp contrast, a biphasic response to the adsorbed surface density of displayed ephrin-B1/Fc was apparent (FIG. 3B). Maximal cell attachment was evoked by surfaces coated with 300 ng/cm² ephrin-B1/Fc (FIG. 3C), and a sharp decline in adsorption was evident at higher densities. This predicts a peak effect at a maximal surface density of $5-18 \times 10^6$ molecules/$\mu^2$ if all adsorbed ligand is active. It is noteworthy that EphB1 receptor activation, determined by phosphotyrosine immunoblot of immunoprecipitated EphB1, was stimulated at adsorption densities greater than 100 ng/cm² and did not show a decrement at densities greater than 300 ng/cm². (A minimum, calculated on the basis of labeled ephrin-B1/Fc recovered from the adsorbed surface is 10 fold lower).

To determine if this ephrin-B1 surface density effect was mediated through integrins, a defined RGD peptide, GRGD-SPK (SEQ ID NO:3), was applied to the surfaces in the absence and presence of ephrin-B1/Fc, or $IgG_1$. Attachment assays of serum-starved microvascular endothelial cells to GRGDSPK (SEQ ID NO:3)-coated 48-well-plates were performed as described herein. Cells were preincubated for 15 min at 22° C. with blocking peptides (100 uM) or anti-integrin antibodies (10 ug/ml) before plating . Similar results were obtained using fibrinogen (1 ug/cm²). HEK293 cells were transiently transfected with pSRα-EphB1 and attachment assays were performed after 48 hours as described herein.

These experiments demonstrated that the RGD peptide was sufficient to support the ephrin-B1 induced increase in endothelial attachment. Moreover, the increase in ephrinB1-induced attachment was sensitive to antibodies that block RGD engagement by $\alpha_v\beta_3$ integrin (LM609), but not $\alpha_v\beta_5$ or $\alpha_5\beta_1$ integrins. Alpha$_v\beta_3$ integrin is an important mediator of endothelial survival, participates in crucial steps in tumor angiogenesis, and has been implicated in angiogenic responses stimulated by bFGF and other angiogenic agonists (49,50).

At the outset, it was not apparent whether ephrin-B1 functions as a mechanical tether in this integrin-mediated increase in endothelial attachment, or as an inducer of signals that activate integrins engagement of extracellular matrix determinants. To address this issue further, a cell line, HEK293, was identified that does not express endogenous EphB1 or EphB2 receptors and that displayed no ephrin-B1 dependent change in attachment to fibrinogen or RGD peptide under basal conditions. Transient expression of EphB1 in HEK293 cells conferred ephrin-B1 dependent increases in attachment to fibrinogen. Antibody competition experiments showed that, in contrast to endothelial cells, ephrin-B1 dependent EphB1 activation in HEK293 cells increased cell attachment through $\alpha_v\beta_1$ integrin, rather than $\alpha_v\beta_3$, which is expressed at very low levels in HEK293. Ephrin-B1 did not increase the surface expression of endothelial $\alpha_v\beta_3$ integrin, or HEK293 $\alpha_5\beta_1$, as assayed by surface protein biotinylation and immunoprecipitation experiments.

Recent reports demonstrated that activated EphB1 receptors recruit Nck and LMW-PTPs through specific tyrosine residues (Y596 and Y929, respectively), and that integrity of receptor tyrosine kinase activity and each of these residues is required for coupling receptor activation to increases in fibronectin attachment. Point mutant EphB1 receptors (Y596F) are defective in binding the SH2 domain of Nck, and in activating c-Jun kinase (51). Residue Y929 in the EphB1 carboxyterminal sterile alpha motif is required for LMW-PTP recruitment (45).

To show that EphB1 tyrosine kinase activity and specific tyrosine residues are required to signal increased attachment through $\alpha_5\beta_1$ integrin, the following experiments were carried out. HEK293 cells were transfected with wild type (wt), kinase inactive (K652R), Nck recruitment defective (Y596F), or LMW-PTP recruitment defective (Y929F) EphB1 expression plasmids. Forty-eight hours after transfection, solid phase attachment assays were conducted on fibrinogen-coated 48-well plates displaying ephrin-B1/Fc (300 ng/cm$^2$), as described herein. Quantitatively similar levels of EphB1 receptor expression were confirmed by immunoblot using monoclonal anti-HA antibody.

These experiments demonstrated that transient HEK293 expression of kinase inactive (K652R), and point mutant EphB1 receptors (Y596F & Y929F), at similar levels, failed to alter $\alpha_5\beta_1$ integrin-mediated attachment. Thus, signaling competent receptors are required to mediate the ephrin-B1 attachment response, and the capacity for receptors to recruit both Nck and LMW-PTP is necessary. Moreover, some change in integrin function, other than surface expression, is required to mediate the response. The ephrin-B1 induced increases in cell attachment appears to reflect "inside-out" activation of $\alpha_5\beta_1$ integrin in HEK293 cells and $\alpha_v\beta_3$ integrin in endothelial cells.

Although the present process has been described with reference to specific details of certain embodiments thereof, it is not intended that such details should be regarded as limitations upon the scope of the invention except as and to the extent that they are included in the accompanying claims.

Throughout this application, various publications are referenced. The disclosures of these publications in their entireties are hereby incorporated by reference into this application in order to more filly describe the state of the art to which this invention pertains.

References

1. Drescher, U., Kremoser, C., Handwerker, C., Loschinger, J., Noda, M. & Bonhoeffer, F. *Cell* 82, 359–370 (1995).
2. Winslow, J. W., Moran, P., Valverde, J., et al. *Neuron* 14, 973–981 (1995).
3. Tessier-Lavigne, M. & Goodman, C. S. *Science* 274, 1123–1133 (1996).
4. Cheng, H. J., Nakamoto, M., Bergemann, A. & Flanagan, J. G. *Cell* 82, 371–378 (1995).
5. Wang, H. U. & Anderson, D. J. *Neuron* 18, 383–396 (1997).
6. Tessier-Lavigne, M. et al. *Cell* 90:403–404 (1997).
7. Pandey, A., Shao, H., Marks, R. M., Polverini, P. J. & Dixit, V. M. *Science* 268, 567–569 (1995).
8. Daniel, T. O., Stein, E., Cerretti, D. P., St.John, P. L., Robert, B. L. & Abrahamson, D. R. *Kidney Int* 50, S-73-S-81 (1996).
9. Beckmann, M. P., Cerretti, D. P., Baum, P., et al. *EMBO Journal* 13, 3757–3762 (1994).
10. Davis, S., Gale, N. W., Aldrich, T. H., et al. *Science* 226, 816–819 (1994).
11. Wo, Y., McCormacks, A. L., Shabanowitz, J., et al. *J Biol Chem* 267, 10856–10865 (1992).
12. Martin, M. M., et al., *In Vitro Cell Dev Biol* 33:261–269 (1997).
13. Bain, G., et al. *BioEssays* 25:343–348 (1994).
14. Brambilla, R., Brueckner, K., Orioli, D., Bergemann, A. D., Flanagan, J. G. & Klein, R. *Mol Cell Neuroscience* 8, 199–209 (1996).
15. Stein, E., Cerretti, D. P. & Daniel, T. O. *J Biol Chem* 271, 23588–23593 (1996).
16. Rigacci, S., Degl'Innocenti, D., Bucciantini, M., Cirri, P., Berti, A. & Ramponi, G. *J Biol Chem* 271, 1278–1281 (1996).
17. Su, X. D., Taddei, N., Stefani, M., Ramponi, G. & Nordlund, P. *Nature* 370, 575–578 (1994).
18. Zhang, M., Stauffacher, C. V. & VanEtten, R. L. *Adv. Prot. Phosphatases* 9, 1–23 (1995).
19. Ostantin, K., Pokalsky, C., Wang, S. & VanEtten, R. L. *J Biol Chem* 270, 18491–18499 (1995).
20. Chiarugi, P., Cirri; P., Raugei, G., et al. *FEBS Letters* 372, 49–53 (1995).
21. Schultz, J., Ponting, C. P., Hofman, K. & Bork, P. *Protein Science* 6, 249–253 (1997).
22. Bohme, B., VandenBos, T., Cerretti, D. P., et al. *J Biol Chem* 271, 24747–24752 (1996).
23. Holland, S. J., Gale, N. W., Mbamalu, G., Yancopoulos, G. D., Henkemeyer, M. & Pawson, T. *Nature* 383, 722–725 (1996).
24. Bruckner, K., Pasquale, E. B. & Klein, R. *Science* 275, 1640–1643 (1997).
25. Henkemeyer, M., Orioli, D., Henderson, J. T., et al. *Cell* 86, 35–46 (1996).
26. Gale, N. W., Flenniken, A., Compton, D. C., et al. *Oncogene* 13, 1343–1352 (1996).
27. Takebe, Y., et al. *Mol Cell Biol.* 8:466–472 (1988).
28. Henkemeyer, M., et al. *Oncogene* 9:1001–1014 (1994)
29. Ingber, D. E. *Proc. Natl. Acad. Sci. USA* 87, 3579–3583 (1990).
30. Cerretti, D. P. et al. *Mol Immun.* 32:1197–1205 (1996).
31. Martin, E. W. (ed.) *Remington's Pharmaceutical Sciences,* latest edition. Mack Publishing Co., Easton, Pa.
32. Risau, et al. "Vasculogenesis" *Ann Rev Cell & Dev Biol* 11:73–91 (1995).
33. Ausprunk, et al. *Microvasc Res* 14:53–65 (1977).
34. Folkman, et al. *Nature Medicine* 1:27–31(1995).
35. Clark and Clark. *Am J Anatomy* 64:251–301 (1939).
36. Cheng and Flanagan. *Cell* 79:157–168 (1994).
37. Nakamoto, et al. *Cell* 86:755–766 (1996).
38. Kozlosky, et al. *Oncogene* 10:299–306 (1995).
39. Gale, et al. *Oncogene* 13:1343–1352 (1996).
40. Dixit, et al. *J Biol Chem* 265:2973–2978 (1990).
41. Brambilla and Klein. *Mol Cell Neurosci* 6:487–495 (1995).
42. Holzman, et al. *Mol Cell Biol* 10:5830–5836 (1990).
43. Folkman, J., et al. *Microvascular Res.* 47:31–40 (1994).
44. Kenyon, B. M., et al. 1996. A model of angiogenesis in the mouse cornea. *Invest. Ophthalmol. Visual Sci.* 37:1625.
45. Stein, E., Lane, A. A., Cerretti, D. P., Schoecklmann, H. O., Schroff, A. D., Van Etten, R. L. & Daniel, T. O. (1998) *Genes Dev.* 12, 667–678.
46. Stein, E., Huynh-Do, U., Lane, A. A., Cerretti, D. P. & Daniel, T. O. (1998) *Journal of Biological Chemistry* 273, 1303–1308.
47. Wang, H. U. & Anderson, D. J. (1997) *Neuron* 18, 383–396.
48. Stein, E., Cerretti, D. P. & Daniel, T. O. (1996) *J Biol Chem* 271, 23588–23593.
49. Freidlander, M., Brooks, P. C., Shaffer, R. W., Kincaid, C. M., Varner, J. A. & Cheresh, D. A. (1995) *Science* 270, 1500–1502.
50. Brooks, P. C., Montgomery, A. M., Rosenfeld, M., Reisfeld, R. A., Hu, T., Klier, G. & Cheresh, D. A. (1994) *Cell* 79,1157–1164.
51. Stein, E., Huynh-Do, U., Lane, A. A., Cerretti, D. P. & Daniel, T. O. (1998) *J Biol Chem.* 273, 1303–1308.

What is claimed is:

1. A method for screening an EphB receptor-binding ligand for the ability to promote a selected biological activity when in multimeric form, comprising:
   a) contacting a multimeric EphB receptor-binding ligand with an EphB receptor-expressing cell under conditions whereby the ligand can bind the receptor; and
   b) detecting the selected biological activity in cells which have bound multimeric ligand as compared to the selected biological activity in cells which have not bound multimeric ligand, whereby a higher level of the selected biological activity in cells which have bound multimeric ligand compared to level of the selected biological activity of cells which have not bound multimeric ligand identifies an EphB receptor-binding ligand with the ability to promote the selected biological activity when in multimeric form.

2. The method of claim 1, wherein the biological activity is selected from the group consisting of cell migration, cell survival, cell targeting and angiogenesis.

3. The method of claim 1, wherein the selected biological activity is the ability to promote cell migration when in multimeric form, comprising:
   a) contacting a multimeric EphB receptor-binding ligand with an EphB receptor-expressing cell under conditions whereby the ligand can bind the receptor; and
   b) detecting migration of cells which have bound multimeric ligand as compared to migration of cells which have not bound multimeric ligand, whereby migration of cells which have bound multimeric ligand and no migration of cells which have not bound multimeric ligand identifies an EphB receptor-binding ligand with the ability to promote cell migration when in multimeric form.

4. The method of claim 1, wherein the selected biological activity is the ability to promote migration, survival and/or targeting of a neural cell multimeric form, comprising:
   a) contacting a multimeric EphB receptor-binding ligand with an EphB receptor-expressing neural cell under conditions whereby the ligand can bind the receptor; and
   b) detecting migration, survival and/or targeting of neural cells which has bound multimeric ligand as compared to migration, survival or targeting of neural cells which has not bound multimeric ligand, whereby migration, survival or targeting of neural cells which has bound multimeric ligand and no migration, survival or targeting of neural cells which has not bound multimeric ligand identifies a ligand with the ability to promote migration, survival or targeting of a neural cells when in multimeric form.

5. A method for screening an EphB receptor for the ability to promote a selected biological activity when the receptor is in multimeric form, comprising:

a) producing a multimeric EphB receptor on the surface of a cell which expresses an EphB receptor; and b) detecting the selected biological activity of cells with a multimeric EphB receptor as compared to the selected biological activity of cells without a multimeric EphB receptor, whereby a higher level of the selected biological activity of cells with a multimeric EphB receptor compared to the level of the selected biological activity of cells without a multimeric EphB receptor identifies an EphB receptor with the ability to promote the selected biological activity when in multimeric form.

6. The method of claim 5, wherein the biological activity is selected from the group consisting of cell migration, cell survival, cell targeting and angiogenesis.

7. The method of claim 5, wherein the selected biological activity is the ability to promote cell migration when the receptor is in multimeric form, comprising:

a) producing a multimeric EphB receptor on the surface of a cell which expresses an EphB receptor; and b) detecting migration of cells with a multimeric EphB receptor as compared to migration of cells without a multimeric EphB receptor, whereby migration of cells with a multimeric EphB receptor and no migration of cells without a multimeric EphB receptor identifies an EphB receptor with the ability to promote cell migration when in multimeric form.

8. The method of claim 5, wherein the selected biological activity is the ability to promote migration, survival and/or targeting of a neural cell when the receptor is in multimeric form, comprising:

a) producing a multimeric EphB receptor on the surface of a neural cell which expresses an EphB receptor; and b) detecting migration, survival or targeting of neural cells with a multimeric EphB receptor as compared to migration, survival or targeting of neural cells without a multimeric EphB receptor, whereby migration, survival and/or targeting of neural cells with a multimeric EphB receptor and no migration, survival or targeting of neural cells without a multimeric EphB receptor identifies an EphB receptor with the ability to promote migration, survival and/or targeting of neural cells when in multimeric form.

* * * * *

UNITED STATES PATENT AND TRADEMARK OFFICE
CERTIFICATE OF CORRECTION

PATENT NO. : 6,555,321 B1
DATED : April 29, 2003
INVENTOR(S) : Daniel et al.

It is certified that error appears in the above-identified patent and that said Letters Patent is hereby corrected as shown below:

<u>Column 1,</u>
Line 7, replace "DK8517" with -- DK38517 --.
Line 7, replace "DK47-48" with -- DK47048 --.

Signed and Sealed this

Third Day of May, 2005

JON W. DUDAS
*Director of the United States Patent and Trademark Office*

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 1

Gly Arg Gly Asp Thr Pro
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 2

Gly Arg Gly Glu Ser Pro
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 3

Gly Arg Gly Asp Ser Pro Lys
1               5
```